United States Patent
Ko et al.

(10) Patent No.: US 10,106,806 B2
(45) Date of Patent: Oct. 23, 2018

(54) TRANSGENIC PLANTS FOR ENHANCING ANTHOCYANIN BIOSYNTHESIS

(71) Applicant: University-Industry Cooperation Group of Kyung Hee University, Gyeonggi-do (KR)

(72) Inventors: Jae Heung Ko, Gyeonggi-do (KR); Jin Seong Cho, Gyeonggi-do (KR); Young Im Choi, Gyeonggi-do (KR); Van Phap Nguyen, Gyeonggi-do (KR)

(73) Assignee: University-Industry Cooperation Group of Kyung Hee University, Gyeonggi-do (KR)

( * ) Notice: Subject to any disclaimer, the term of this patent is extended or adjusted under 35 U.S.C. 154(b) by 9 days.

(21) Appl. No.: 15/353,946

(22) Filed: Nov. 17, 2016

(65) Prior Publication Data

US 2017/0211079 A1 Jul. 27, 2017

(30) Foreign Application Priority Data

Nov. 17, 2015 (KR) .................. 10-2015-0161304

(51) Int. Cl.
*C12N 15/82* (2006.01)
*A01H 5/00* (2018.01)

(52) U.S. Cl.
CPC ............. *C12N 15/825* (2013.01); *A01H 5/00* (2013.01)

(58) Field of Classification Search
CPC ....... C12N 15/825; C07K 14/415; A01H 5/00
See application file for complete search history.

(56) References Cited

FOREIGN PATENT DOCUMENTS

| KR | 10-2010-0022553 | 3/2010 |
| KR | 10-2010-0103189 | 9/2010 |
| KR | 10-2014-0126528 | 10/2014 |

OTHER PUBLICATIONS

Wilkins O, Nahal H, Foong J, Provart NJ, Campbell MM (2009) Expansion and diversification of the Populus R2E3-MYB family of transcription factors. Plant Physiol 149:981-993. (Year: 2009).*
Gonzalez, A., Zhao, M., Leavitt, J.M., and Lloyd, A.M. (2008). Regulation of the anthocyanin biosynthetic pathway by the TTG1/bHLH/Myb transcriptional complex in *Arabidopsis* seedlings. Plant J. 53:814-827 (Year: 2008).*
Shi, Ming-Zhu, and De-Yu Xie. "Features of anthocyanin biosynthesis in pap1-D and wild-type *Arabidopsis thaliana* plants grown in different light intensity and culture media conditions." Planta 231.6 (2010): 1385-1400. (Year: 2010).*
Wilkins O, Nahal H, Foong J, Provart NJ, Campbell MM (2009) Expansion and diversification of the Populus R2R3-MYB family of transcription factors. Plant Physiol 149:981-993. (Year: 2009).*
Wilkins et al "Expansion and Diversification of the Populus R2R3-MYB Family of Transcription Factors" Plant Physiology vol. 149, pp. 981-993, 2009.
Cho, et al., "Functional characterization of R2R3-MYB transcription factors that activate anthocyanin pigment production in hybrid poplars", 2015 International Symposium on Plant Sciences & Annual Conference of the Korean Society of Plant Biologics.
Cho, et al., "Molecular characterization of PtrPAP1 functions as a transcriptional activator of anthocyanin pigment production in Populus", KFRI Tree Biotechnology Symposium 2015.
Cho, et al., "Overexpression of PtrMYB119, a R2R3-MYB transcription factor from Populus trichocarpa, promotes anthocyanin production in hybrid poplar", Tree Physiology, 36, 1162-1176, 2016.
Christie, et al., "Impact of low-temperature stress on general phenylpropanoid and anthocyanin pathways: Enhancement of transcript abundance and anthocyanin pigmentation in maize seedlings", Planta (1994) 194:541-549.
Holton, et al., "Genetics and Biochemistry of Ant hocyanin Biosynthesis", The Plant Cell, vol. 7, 1071-1083, Jul. 1995.
Mancinelli, "Interaction between Light Quality and Light Quantity in the Photoregulation of Anthocyanin Production", Plant Physiol. (1990) 92, 1191-1195.

* cited by examiner

*Primary Examiner* — Lee A Visone
*Assistant Examiner* — Weihua Fan
(74) *Attorney, Agent, or Firm* — Cesari and McKenna, LLP

(57) ABSTRACT

The present invention relates to a transgenic plant with enhanced anthocyanin biosynthesis by the introduction of PtrMYB119 gene operably linked to a promoter, a method for preparing the transgenic plant, a method for producing anthocyanin from the transgenic plant, a composition for promoting anthocyanin biosynthesis comprising PtrMYB119 gene operably linked to a promoter, a kit for promoting anthocyanin biosynthesis comprising the composition, and a method for enhancing anthocyanin biosynthesis in a plant comprising introducing the composition into a plant for its expression. The use of the composition for enhancing anthocyanin biosynthesis provided in the present invention enables large-scale production of anthocyanins without any affect on the growth of the plant cell, which is a host, and thus the composition can be widely used for more effective production of anthocyanins.

12 Claims, 16 Drawing Sheets
Specification includes a Sequence Listing.

[Figure 1A]
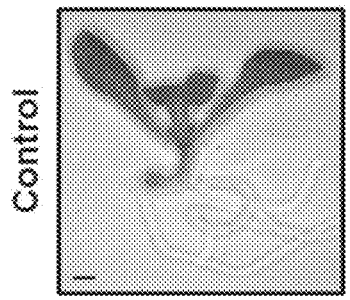
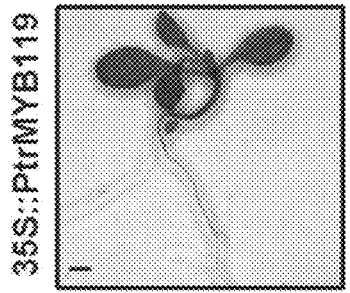
[Figure 1B]
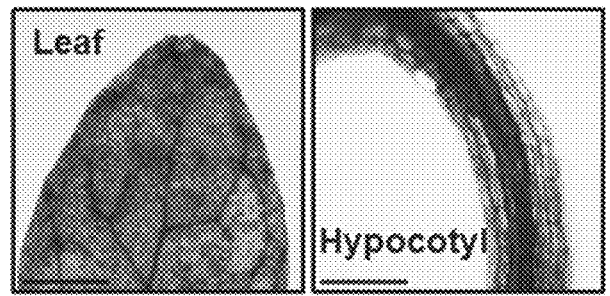
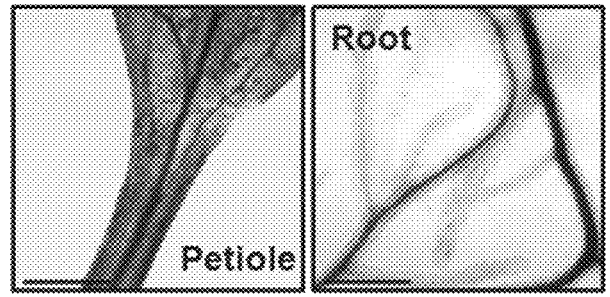

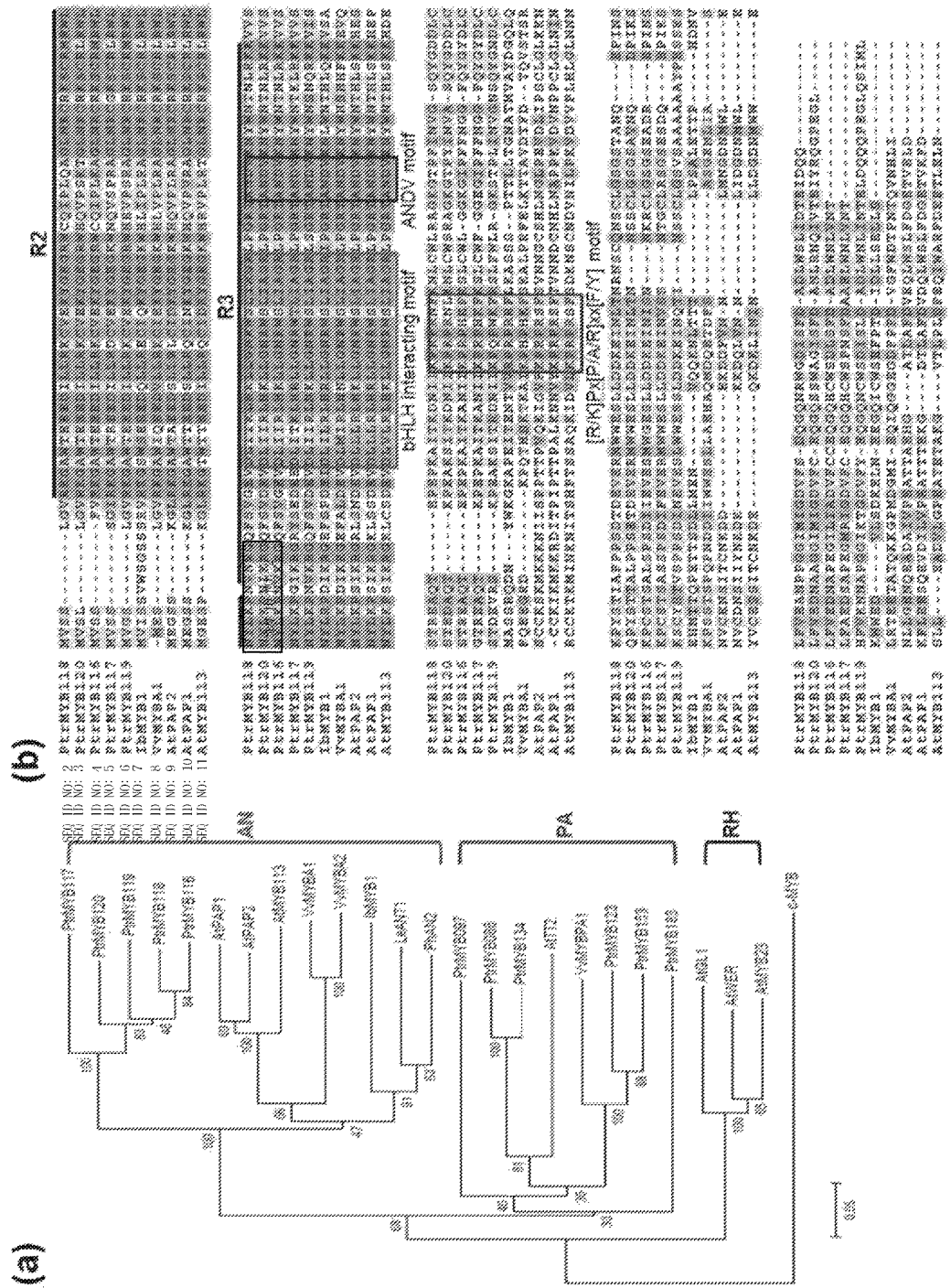
[Figure 2]

[Figure 3A]
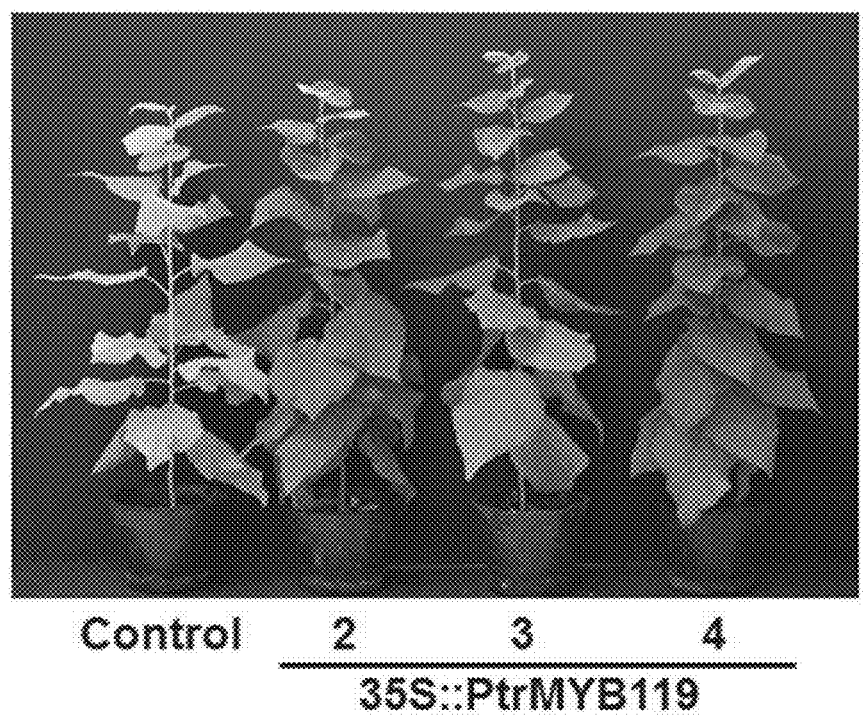
[Figure 3B]
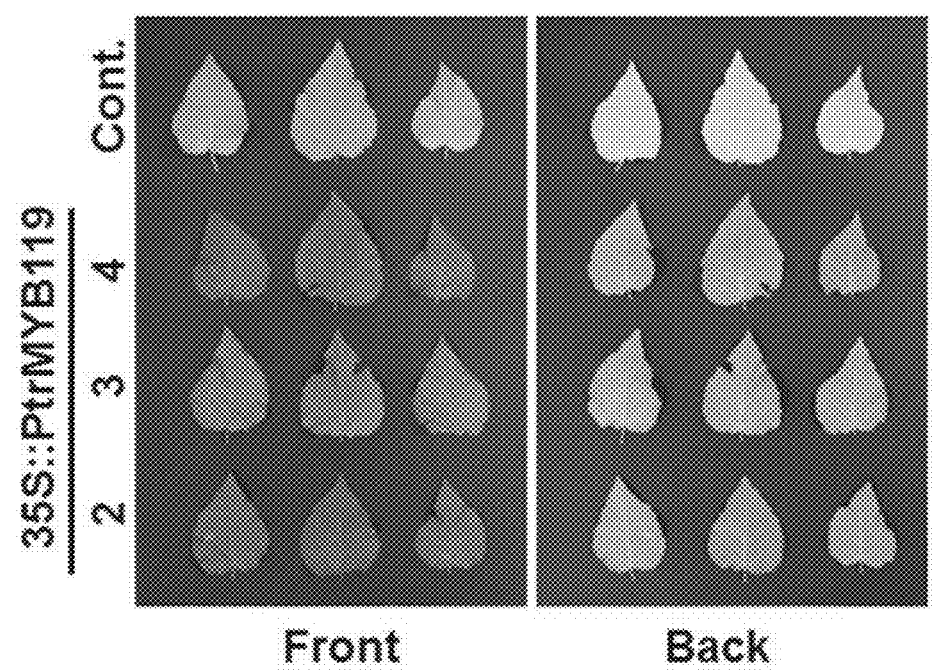

[Figure 3C]
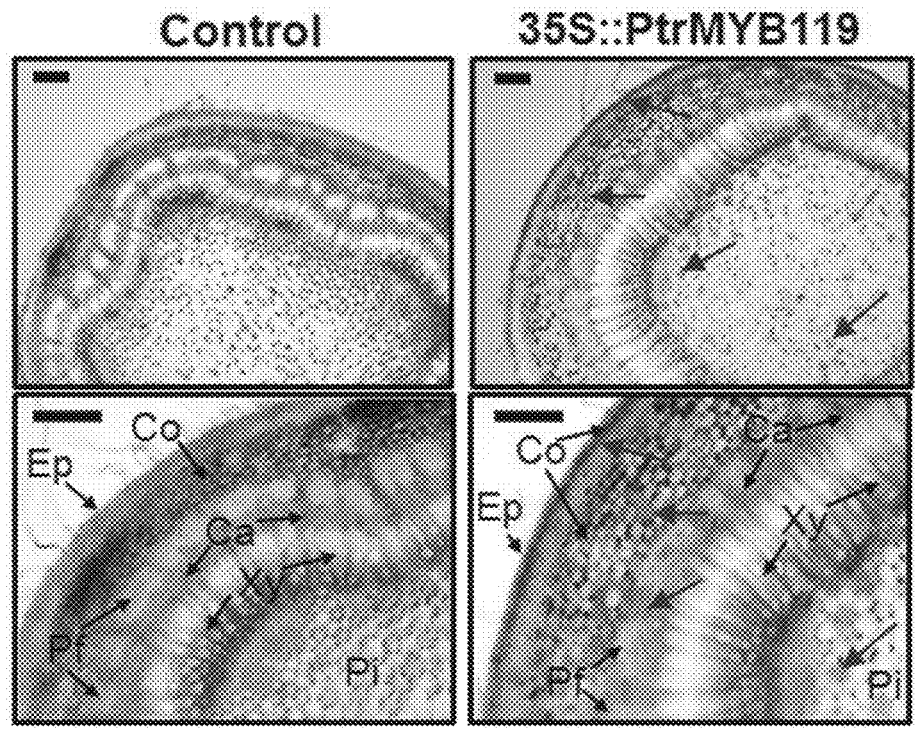
[Figure 3D]
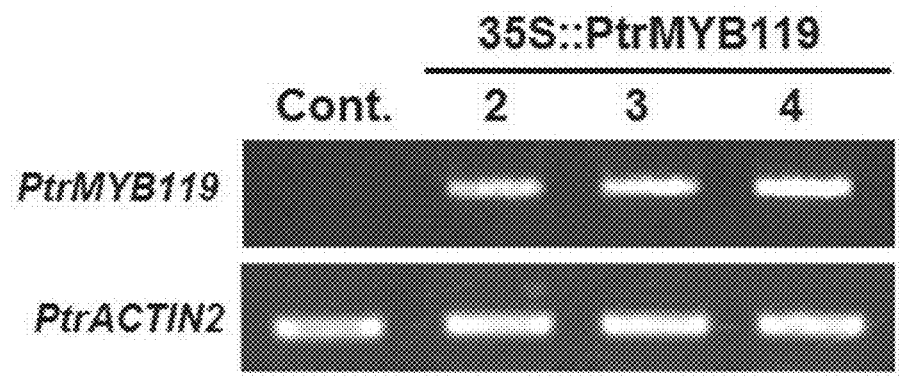

[Figure 3E]
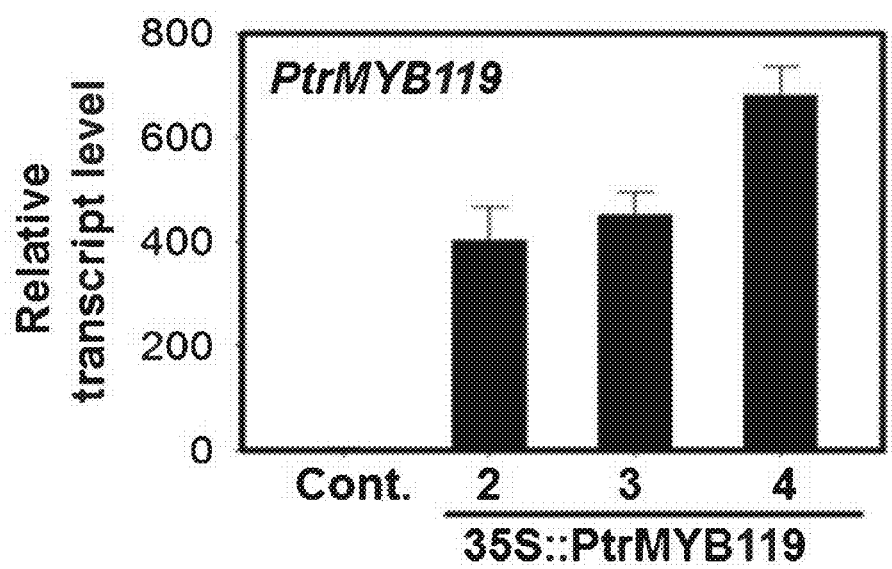

[Figure 4A]
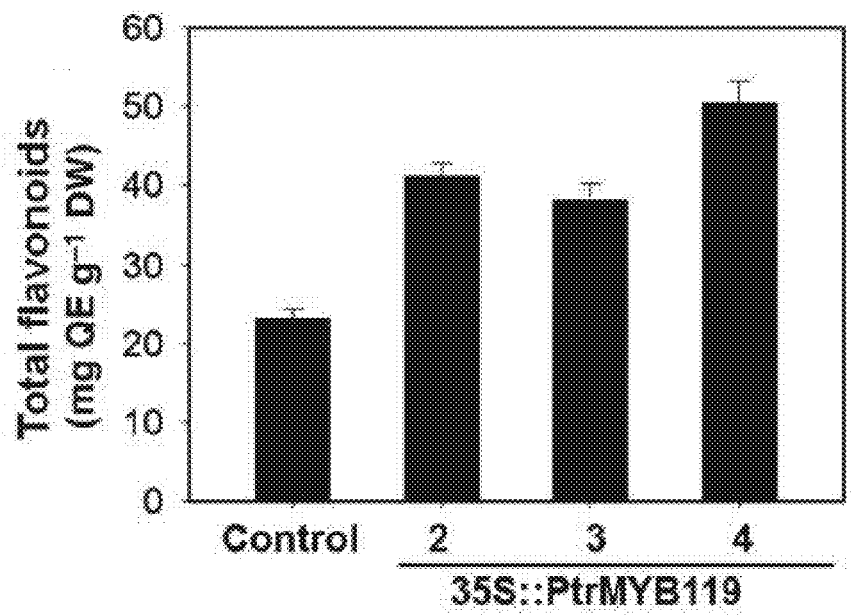
[Figure 4B]
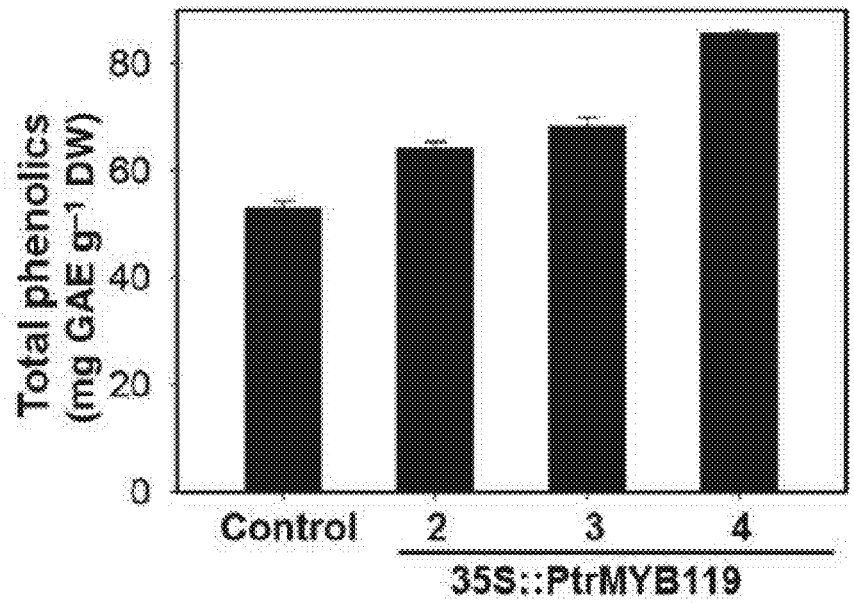

[Figure 5]
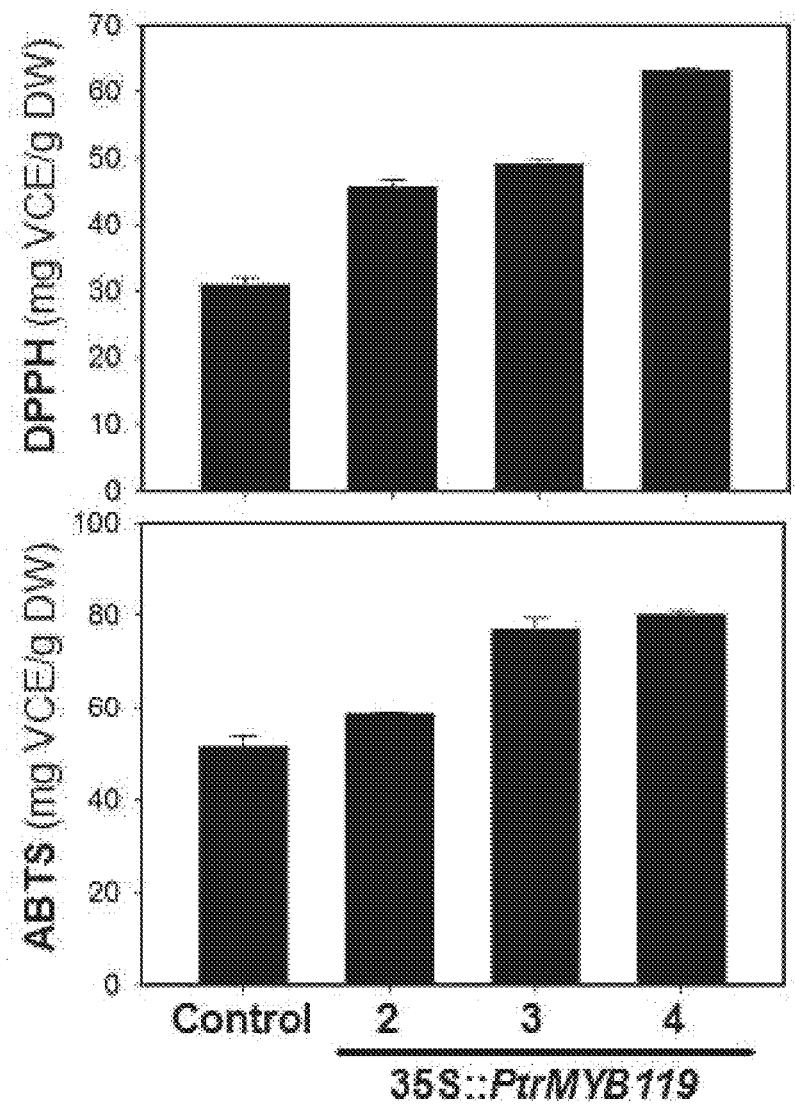

[Figure 6A]
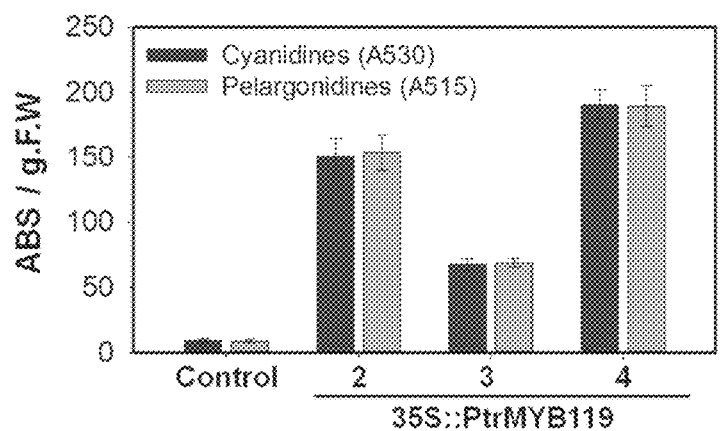
[Figure 6B]
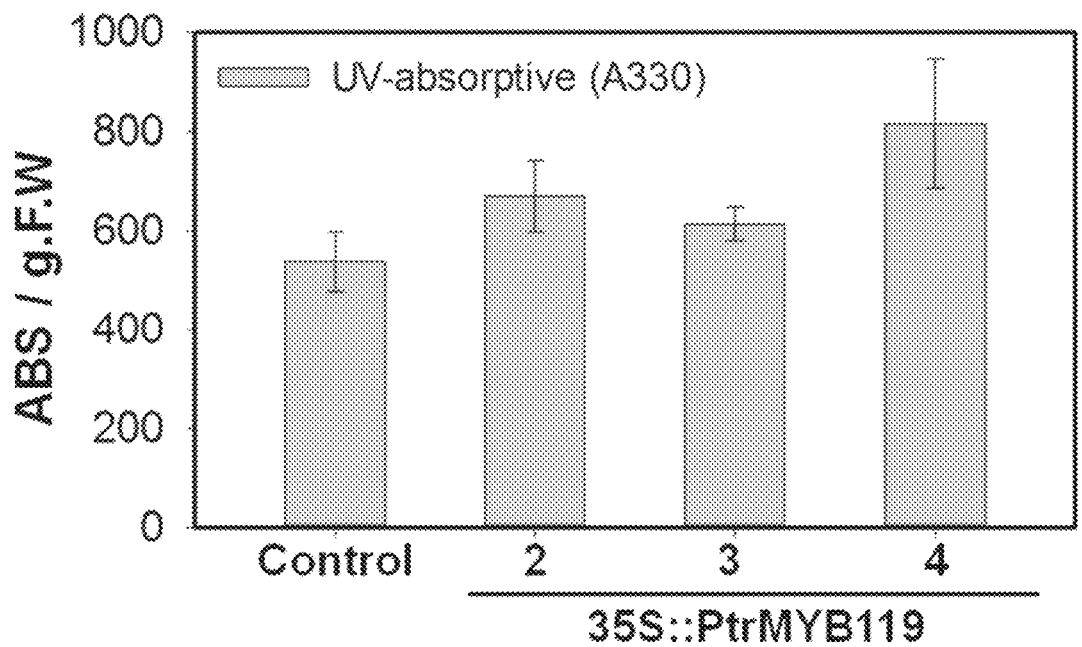

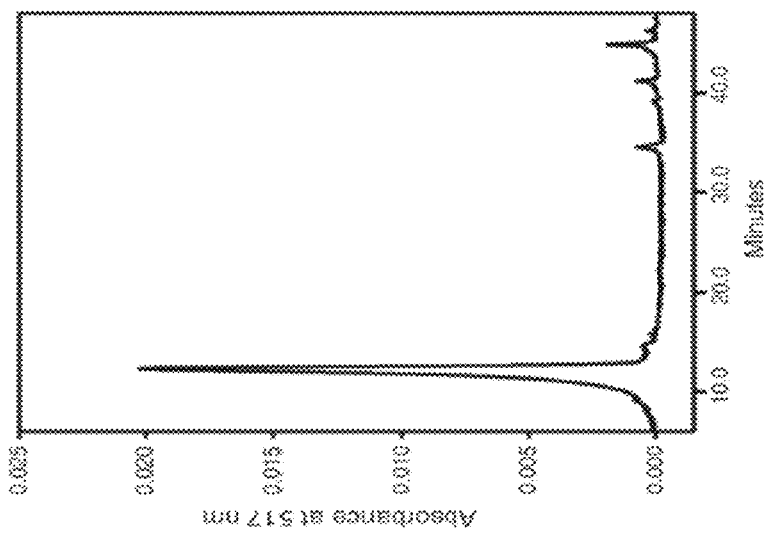
[Figure 7A]
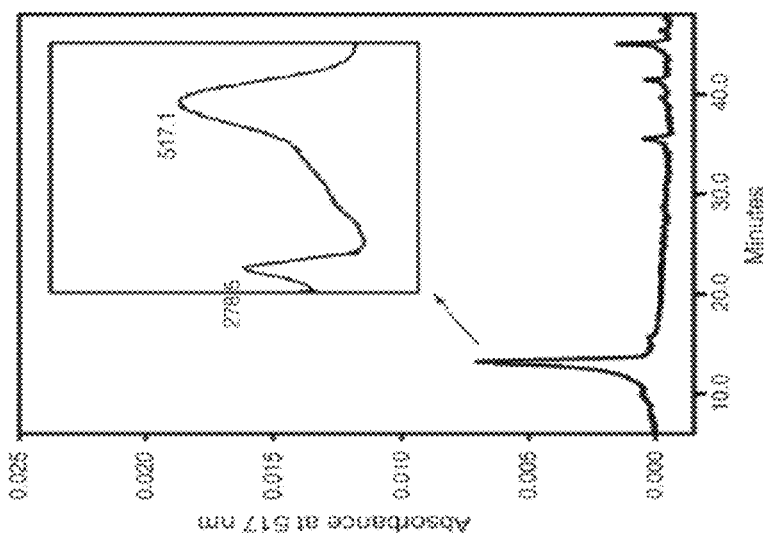
[Figure 7B]
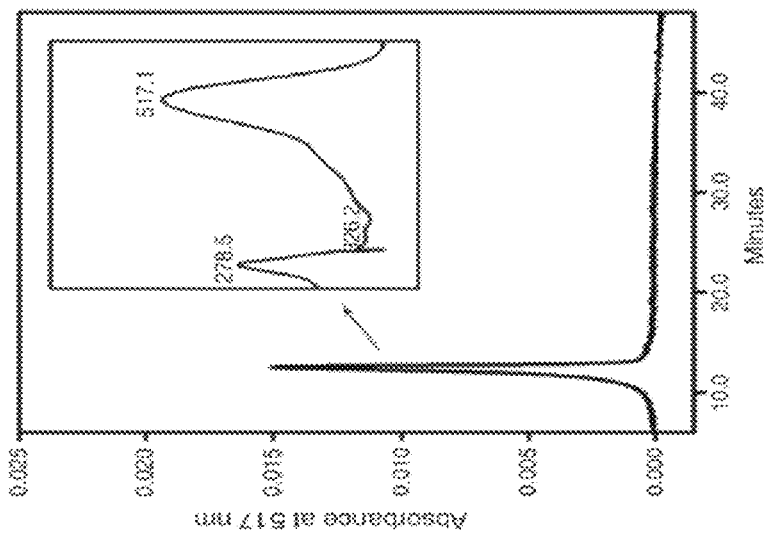
[Figure 7C]

[Figure 8A]
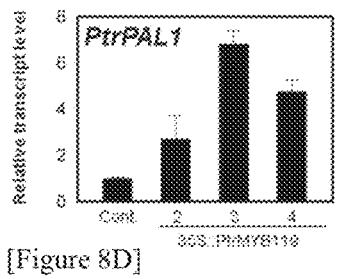
[Figure 8B]
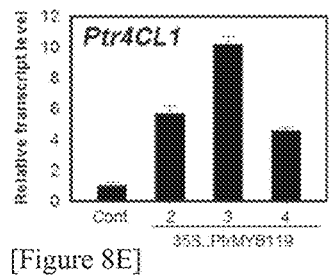
[Figure 8C]
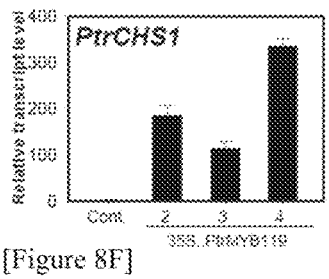
[Figure 8D]
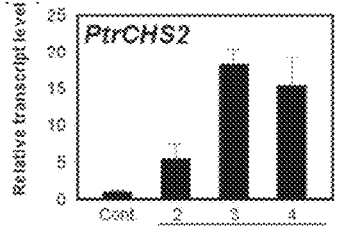
[Figure 8E]
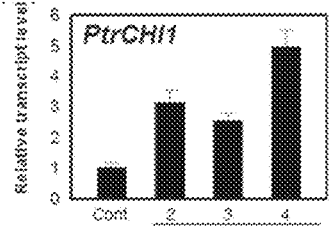
[Figure 8F]
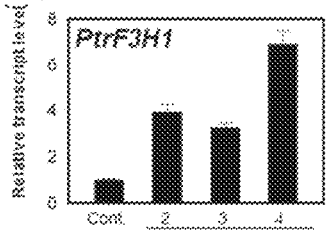
[Figure 8G]
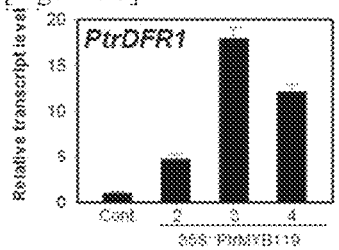
[Figure 8H]
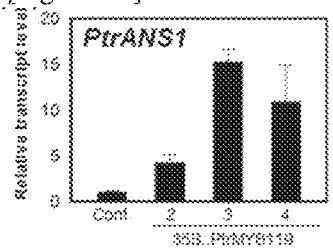
[Figure 8I]
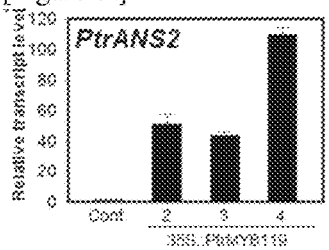
[Figure 8J]
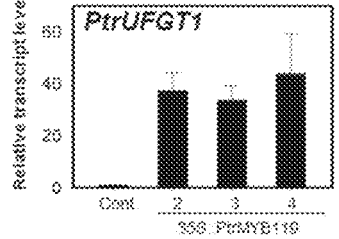
[Figure 8K]
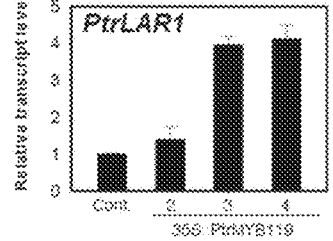
[Figure 8L]
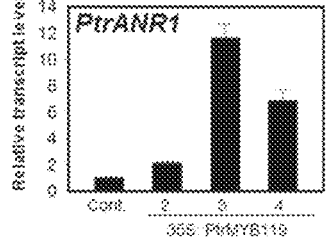

[Figure 9A]
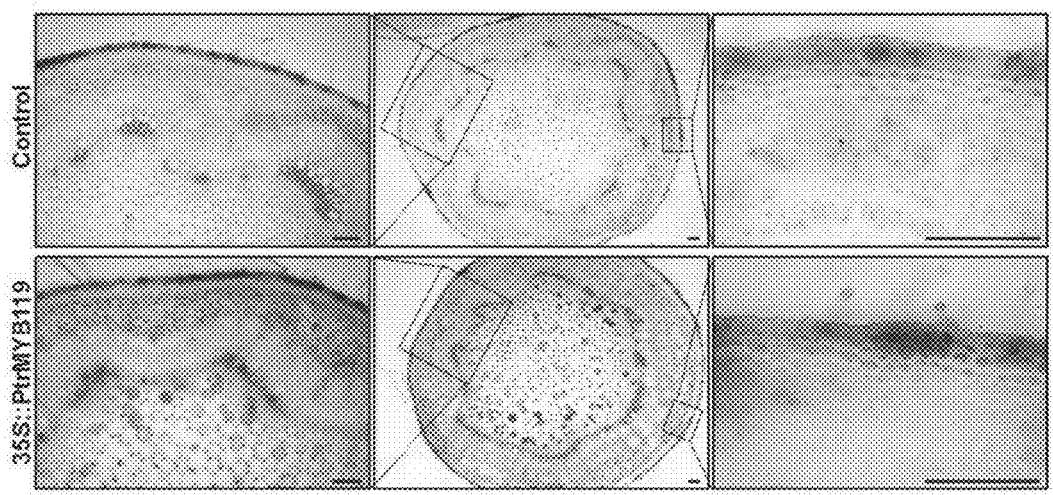
[Figure 9B]
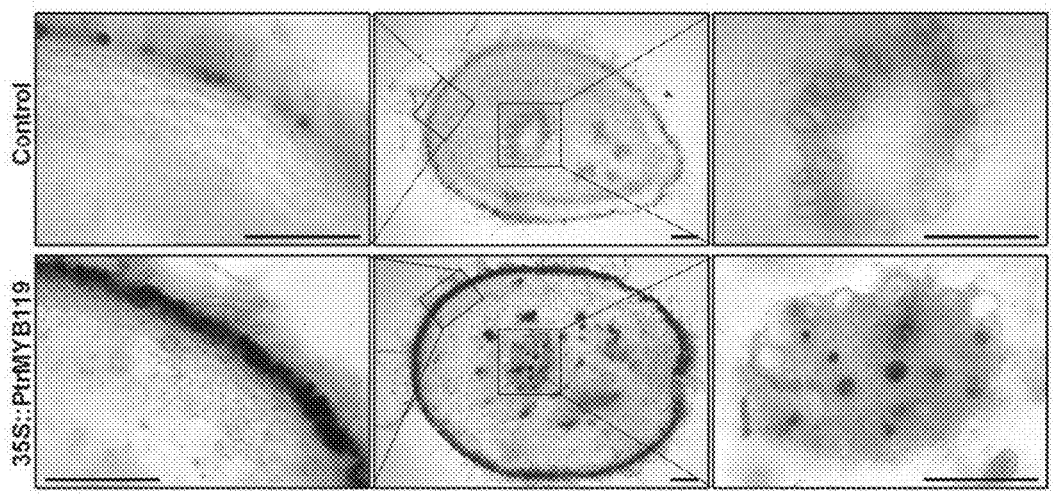

[Figure 10A]
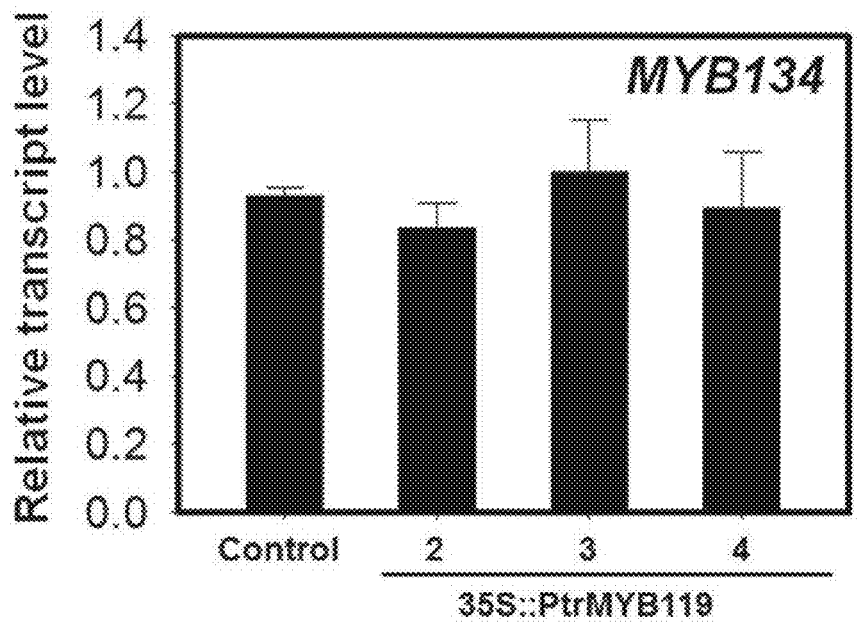
[Figure 10B]
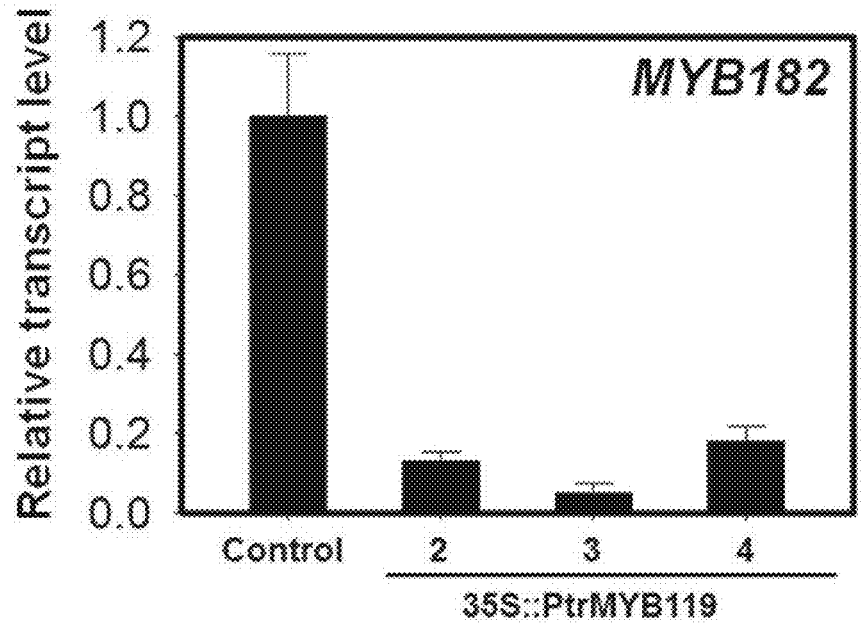

[Figure 11A]
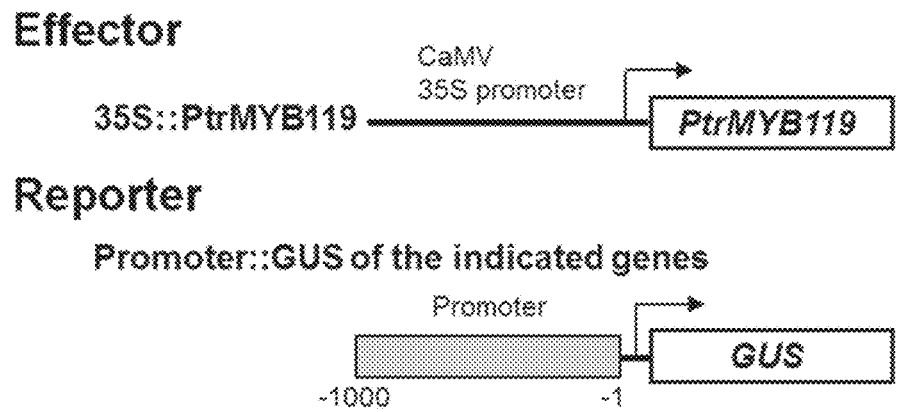
[Figure 11B]
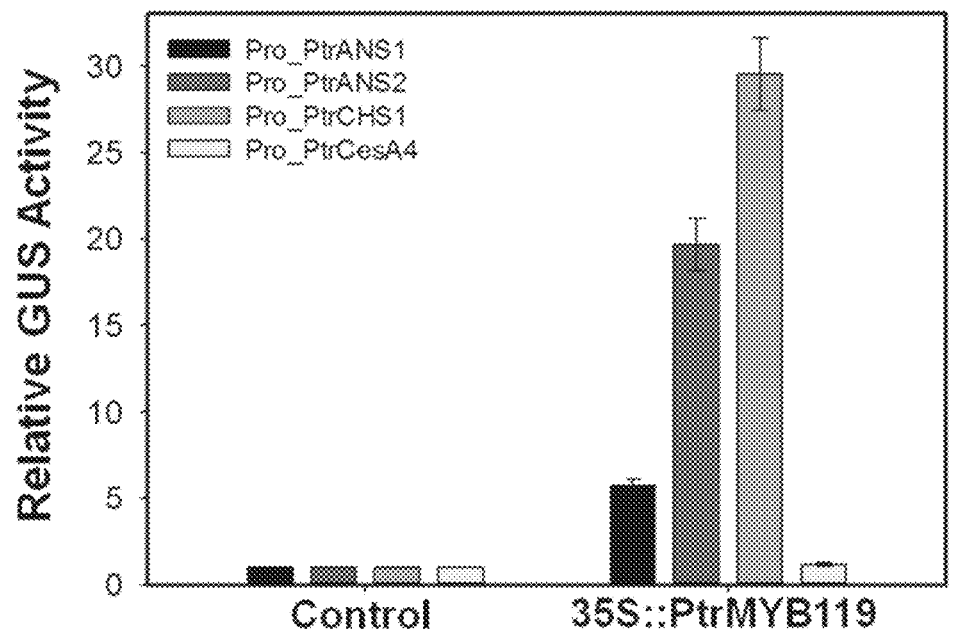

[Figure 12A]
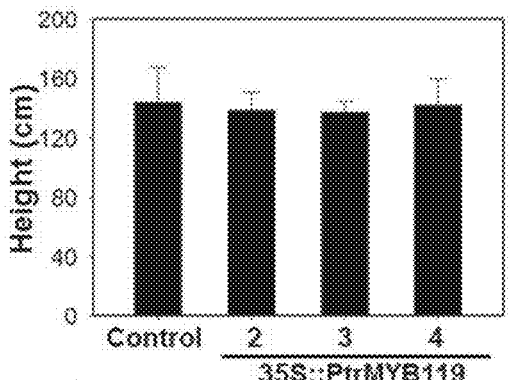
[Figure 12B]
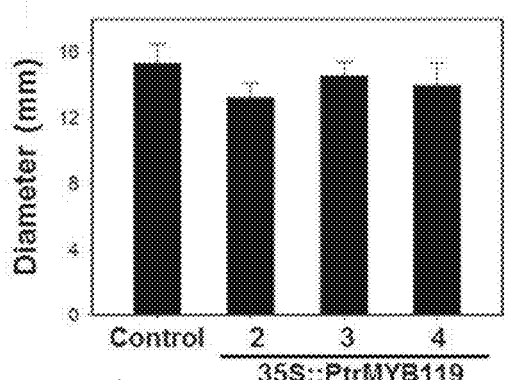
[Figure 12C]
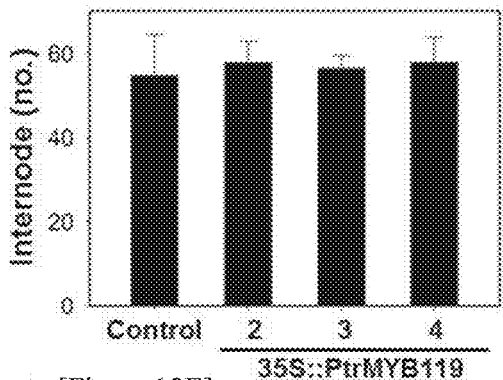
[Figure 12D]
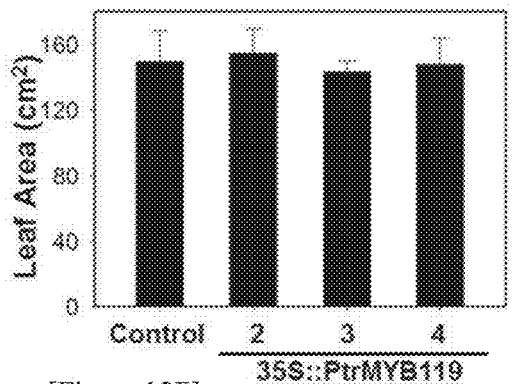
[Figure 12E]
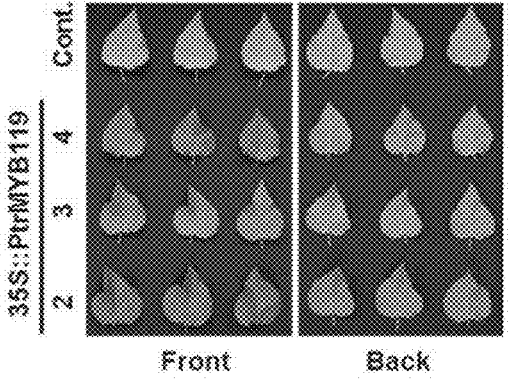
[Figure 12F]
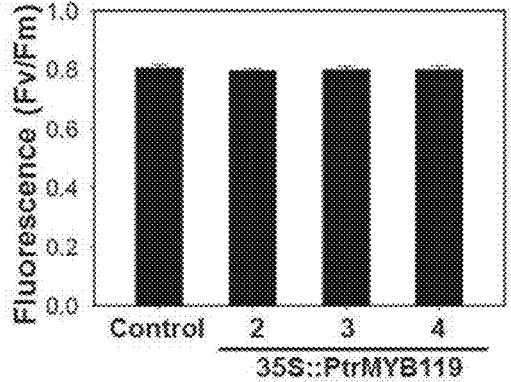

[Figure 13]
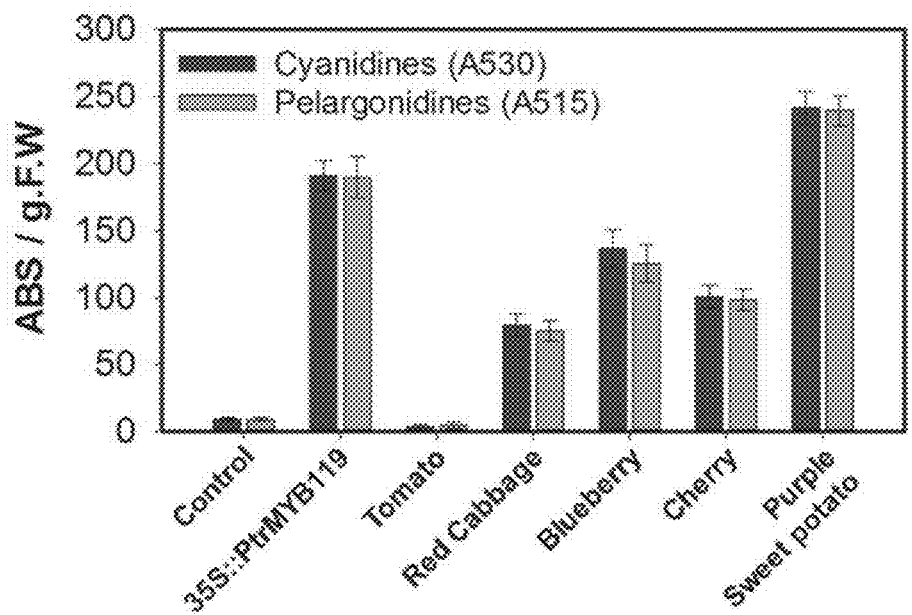
[Figure 14]
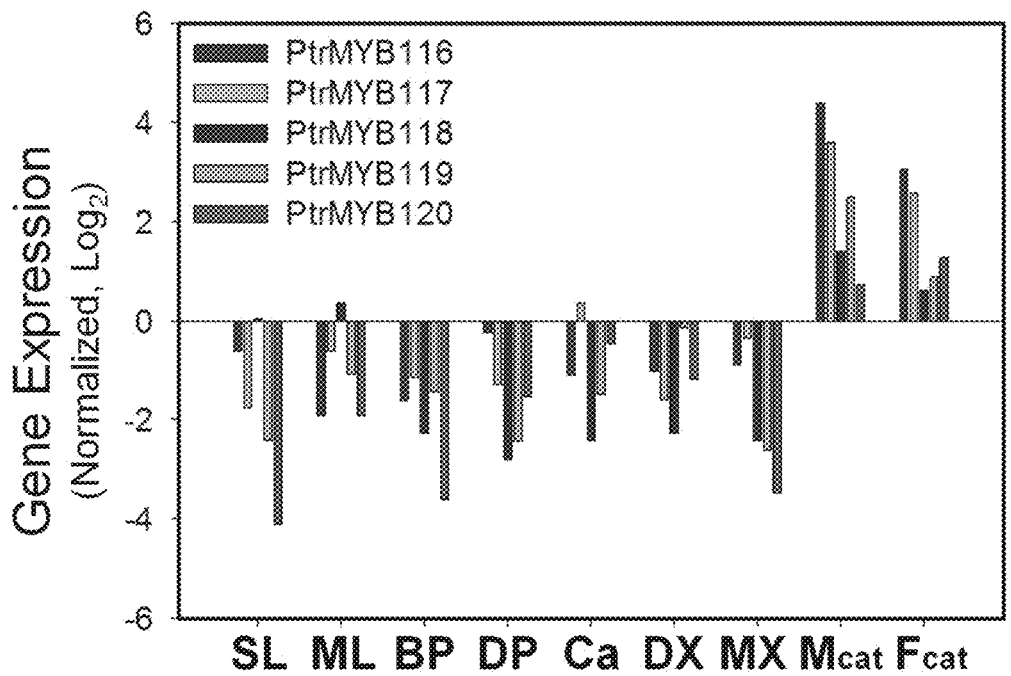

[Figure 15A]
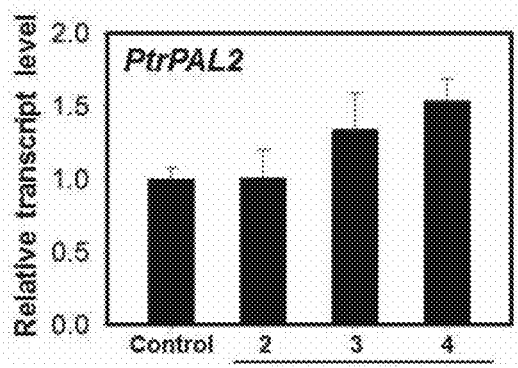
[Figure 15B]
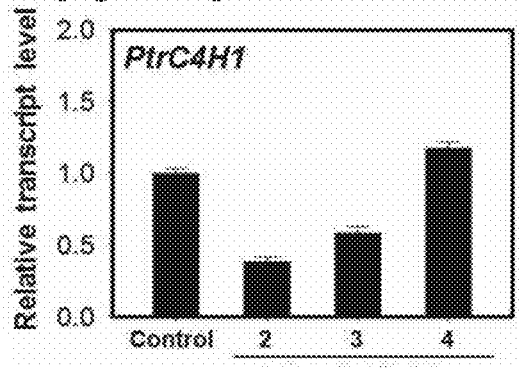
[Figure 15C]
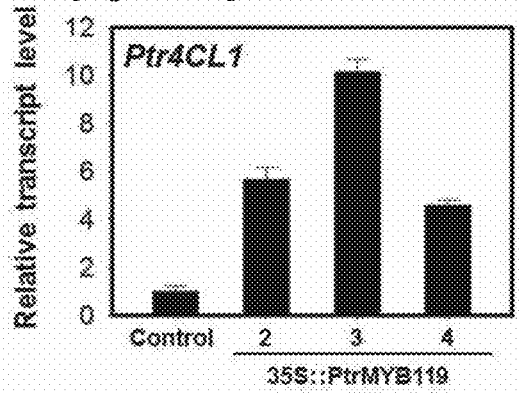

SEQUENCE LISTING

```
<160> NUMBER OF SEQ ID NOS: 60

<210> SEQ ID NO 1
<211> LENGTH: 834
<212> TYPE: DNA
<213> ORGANISM: Artificial sequence
<220> FEATURE:
<223> OTHER INFORMATION: recombinant PtrMYB119 gene

<400> SEQUENCE: 1
atggtaggct cattaggagt aaggaaaggt gcatggacgg aggaggaaga tatacttcta      60
aggaagtgcg tcgagaaata tggtgaagga agatggcatg aagttccttc cagagcaggc     120
ttgaatcgat gcaggaaaag ctgcagaatg aggtggttga attatcttaa gccaaatgtc     180
aagagaggac agtttccggt ggacgaagtg gacttgatta tcagactaca caagttgctt     240
ggcaataggt ggtcattgat agctggtaga ctttcaggaa gaacagcgaa tgatgtcaag     300
```

```
aattattgga actcaaacca gcgtaagaag gtgatttcta gcactgatga agttcgatca      360
aaaccagaag caaaatcaat cacaagagac aacataataa agcctcaacc ttggaagttc      420
agaagtttat tctggttaag aggaaaaagt actccactta ttaatgttgg taattctcaa      480
tatgggaacg atctttgtaa gtcatgttat tcaacagtat cgccaccttc cgacattaat      540
gaagttgaaa gtttatggtg ggaaagctcg ttagatgaca agaaattaa tcaaacgatc       600 aacagcagtt gtctgggttc tgtttcagca gcagcagcag cagcttaccc agagtccagc      660
gaaagtcatt ttgtaaagaa caacgcacca ggagggataa aaactgggga cgtgttctat      720
gaacaaggac aaaattgttg gagtgacatt tctttggatg cagacctttg aatctaatc       780 aatacagaac tagatcaaca acaacctgaa ggacttcagt ctataatgtt gtaa            834
```

<210> SEQ ID NO 2
<211> LENGTH: 267
<212> TYPE: PRT
<213> ORGANISM: Populus balsamifera subsp. trichocarpa
<220> FEATURE:
<221> NAME/KEY: MISC_FEATURE
<223> OTHER INFORMATION: PtrMYB118

<400> SEQUENCE: 2

```
Met Val Ser Ser Leu Gly Val Arg Lys Gly Ala Trp Thr Glu Glu
1               5                   10                  15

Asp Ile Leu Leu Arg Lys Cys Val Glu Lys Tyr Gly Glu Gly Arg Trp
            20                  25                  30

Cys Gln Ile Pro Leu Gln Ala Gly Leu Asn Arg Cys Arg Lys Ser Cys
        35                  40                  45

Arg Met Arg Trp Leu Asn Tyr Leu Lys Pro Asn Val Asn Arg Gly Gln
    50                  55                  60

Phe Ser Val Gly Glu Val Asp Leu Ile Ile Arg Leu His Lys Leu Leu
65                  70                  75                  80

Gly Asn Arg Trp Ser Leu Ile Ala Gly Arg Leu Pro Gly Arg Thr Ala
                85                  90                  95

Asn Asp Val Lys Asn Tyr Trp Asn Thr Asn Leu Arg Lys Lys Val Val
            100                 105                 110

Ser Ser Thr Arg Glu Ala Gln Thr Glu Pro Glu Pro Lys Ala Ile Thr
        115                 120                 125

Lys Asp Asn Ile Ile Lys Pro Arg Pro Arg Asn Phe Lys Asn Leu Cys
    130                 135                 140

Trp Leu Arg Ala Gly Lys Gly Thr Pro Phe Ile Asn Val Gly Ser Gln
145                 150                 155                 160

Tyr Gly Asp Asp Leu Cys Lys Pro Tyr Ser Thr Ile Ala Phe Pro Pro
                165                 170                 175

Ser Asp Thr Asp Glu Val Glu Arg Met Trp Trp Glu Ser Leu Leu Asp
            180                 185                 190

Asp Lys Glu Ile Asn Leu Thr Asn Arg Asn Ser Cys Gln Asn Ser Cys
        195                 200                 205

Leu Gly Ser Gly Ser Thr Ala Asn Gln Glu Pro Ile Asn Ser Leu Phe
    210                 215                 220

Val Glu Ala Asn Pro Pro Gly Gly Ile Met Ile Gly Asp Val Phe Ser
225                 230                 235                 240

Asp Gln Gly Gln Asn Arg Trp Gly Asp Ile Ser Phe Asp Ala Asp Leu
                245                 250                 255

Trp Ser Leu Ile Asp Thr Glu Ile Asp Gln Gln
            260                 265
```

260             265

<210> SEQ ID NO 3
<211> LENGTH: 268
<212> TYPE: PRT
<213> ORGANISM: Populus balsamifera subsp. trichocarpa
<220> FEATURE:
<221> NAME/KEY: MISC_FEATURE
<223> OTHER INFORMATION: PtrMYB120

<400> SEQUENCE: 3

Met Val Ser Leu Leu Gly Val Arg Lys Gly Ala Trp Thr Glu Glu
1               5                   10                  15

Asp Ile Leu Leu Arg Lys Cys Val Glu Lys Tyr Gly Glu Gly Arg Trp
            20                  25                  30

His Gln Val Pro Ser Lys Thr Gly Leu Asn Arg Cys Arg Lys Ser Cys
        35                  40                  45

Arg Leu Arg Trp Leu Asn Tyr Leu Lys Pro Asn Ile Lys Arg Gly Gln
    50                  55                  60

Phe Ser Val Asp Glu Val Asp Leu Ile Ile Arg Leu His Lys Leu Leu
65                  70                  75                  80

Gly Asn Arg Trp Ser Leu Ile Ala Gly Arg Leu Pro Gly Arg Thr Ala
                85                  90                  95

Asn Asp Val Lys Asn Tyr Trp Asn Thr Asn Leu Arg Lys Lys Val Val
            100                 105                 110

Ser Ser Thr Glu Asp Ala Gln Thr Lys Pro Glu Ala Lys Ser Ile Thr
        115                 120                 125

Lys Asp Asn Ile Ile Lys Pro Arg Pro Arg Asn Leu Lys Asn Leu Cys
    130                 135                 140

Trp Ser Arg Ala Gly Lys Gly Thr Pro Tyr Ile Asn Val Ala Ser Gln
145                 150                 155                 160

Tyr Gly Asp Asp Leu Cys Gln Pro Tyr Ser Thr Thr Ala Leu Pro Pro
                165                 170                 175

Ser Glu Thr Asp Glu Val Glu Arg Met Trp Trp Glu Ser Leu Leu Asp
            180                 185                 190

Asp Lys Glu Ile Asn Leu Thr Asn Asn Ser Ser Cys Leu Gly Ser Gly
        195                 200                 205

Ser Ala Val Asn Gln Asp Pro Ile Lys Ser Leu Phe Val Glu Asp Asn
    210                 215                 220

Ala Ala Gly Gly Ile Met Ile Gly Asp Val Phe Cys Glu Gln Gly Gln
225                 230                 235                 240

Ser Ser Trp Ala Gly Ile Ser Phe Asp Ala Asn Leu Arg Asn Gln Ile
                245                 250                 255

Val Thr Glu Ile Tyr Arg Gln Gly Pro Glu Gly Leu
            260                 265

<210> SEQ ID NO 4
<211> LENGTH: 257
<212> TYPE: PRT
<213> ORGANISM: Populus balsamifera subsp. trichocarpa
<220> FEATURE:
<221> NAME/KEY: MISC_FEATURE
<223> OTHER INFORMATION: PtrMYB116

<400> SEQUENCE: 4

Met Val Ser Ser Phe Val Arg Lys Gly Ala Trp Thr Glu Glu Asp
1               5                   10                  15

Ile Leu Leu Arg Lys Cys Val Glu Lys Tyr Gly Glu Gly Arg Trp Cys

```
                20              25                  30
Gln Ile Pro Lys Ala Gly Leu Asn Arg Cys Arg Lys Ser Cys Arg
            35                  40                  45
Met Arg Trp Leu Asn Tyr Leu Lys Pro Asn Val Asn Arg Gly Gln Phe
    50                  55                  60
Ser Val Gly Glu Val Asp Leu Ile Ile Arg Leu His Lys Leu Leu Gly
65                  70                  75                  80
Asn Arg Trp Ser Leu Ile Ala Gly Arg Leu Pro Gly Arg Thr Ala Asn
                85                  90                  95
Asp Val Lys Asn Tyr Trp Asn Thr Asn Leu Arg Lys Lys Val Val Ser
            100                 105                 110
Ser Thr Arg Glu Ala Gln Thr Glu Pro Glu Pro Lys Ala Ile Thr Lys
            115                 120                 125
Ala Asn Ile Ile Lys Pro Arg Pro His Lys Phe Lys Ser Leu Cys Trp
            130                 135                 140
Leu Gly Gly Lys Gly Ile Pro Phe Phe Asn Gly Gly Phe Gln Tyr Gly
145                 150                 155                 160
Tyr Asp Leu Cys Lys Pro Cys Ser Thr Ser Ala Leu Ser Pro Ser Asp
                165                 170                 175
Ile Ile Glu Val Glu Ser Met Trp Gly Glu Ser Leu Leu Asp Asp Lys
            180                 185                 190
Glu Ile Asn Ile Ser Asn Asn Lys Arg Cys Leu Gly Ser Gly Ser Glu
            195                 200                 205
Ala Asp Arg Glu Pro Ile Asn Ser Leu Phe Val Glu Asp Asn Ala Pro
            210                 215                 220
Glu Gly Ile Leu Ile Ala Asp Val Phe Cys Cys Glu Gln Gly Gln His
225                 230                 235                 240
Cys Trp Asp Ser Leu Ser Phe Asp Ala Asp Leu Trp Asn Leu Tyr Asn
                245                 250                 255
Thr

<210> SEQ ID NO 5
<211> LENGTH: 258
<212> TYPE: PRT
<213> ORGANISM: Populus balsamifera subsp. trichocarpa
<220> FEATURE:
<221> NAME/KEY: MISC_FEATURE
<223> OTHER INFORMATION: PtrMYB117

<400> SEQUENCE: 5

Met Val Ser Ser Gly Ile Arg Lys Gly Ala Trp Thr Arg Glu Glu
1               5                   10                  15
Asp Ile Leu Leu Arg Asp Cys Val Glu Lys Tyr Gly Glu Gly Lys Trp
            20                  25                  30
Asn Gln Val Ser Pro Arg Ala Gly Leu Asn Arg Cys Gly Lys Ser Cys
            35                  40                  45
Arg Leu Arg Trp Leu Asn Tyr Leu Lys Pro Gly Ile Lys Arg Gly Arg
    50                  55                  60
Tyr Ser Glu Asp Glu Asp Leu Ile Thr Lys Leu His Arg Leu Leu
65                  70                  75                  80
Gly Asn Arg Trp Thr Leu Ile Ala Gly Arg Leu Pro Gly Arg Thr Ala
                85                  90                  95
Asn Asp Val Lys Asn Tyr Trp Asn Thr Lys Leu Arg Lys Lys Val Val
            100                 105                 110
Ser Gly Thr Arg Glu Ala Gln Thr Lys Pro Glu Pro Lys Ala Ile Thr
```

```
            115                 120                 125
Lys Ala Asn Ile Ile Lys Pro Arg Pro His Lys Phe Lys Ser Leu Cys
    130                 135                 140

Trp Phe Gly Gly Glu Gly Ile Pro Phe Phe Asn Gly Gly Phe Gln Tyr
145                 150                 155                 160

Gly Tyr Asp Leu Cys Lys Pro Cys Ser Thr Ser Ala Ser Ser Pro Ser
                165                 170                 175

Asp Ile Phe Glu Val Glu Arg Met Trp Trp Glu Ser Leu Leu Asp Asp
            180                 185                 190

Lys Glu Ile Asn Val Ser Ser Asn Thr Gly Cys Leu Arg Ser Gly Ser
        195                 200                 205

Glu Ser Asp Gln Glu Pro Ile Lys Ser Leu Phe Ala Glu Asp Ser Ala
210                 215                 220

Pro Glu Gly Met Arg Ile Gly Asp Val Phe Cys Glu Gln Gly Gln His
225                 230                 235                 240

Cys Trp Ser Pro Asn Ser Phe Asp Ala Ala Glu Leu Trp Asn Leu Val
                245                 250                 255

Asn Thr

<210> SEQ ID NO 6
<211> LENGTH: 277
<212> TYPE: PRT
<213> ORGANISM: Populus balsamifera subsp. trichocarpa
<220> FEATURE:
<221> NAME/KEY: MISC_FEATURE
<223> OTHER INFORMATION: PtrMYB119

<400> SEQUENCE: 6

Met Val Gly Ser Leu Gly Val Arg Lys Gly Ala Trp Thr Glu Glu
1               5                   10                  15

Asp Ile Leu Leu Arg Lys Cys Val Glu Lys Tyr Gly Glu Gly Arg Trp
            20                  25                  30

His Glu Val Pro Ser Arg Ala Gly Leu Asn Arg Cys Arg Lys Ser Cys
        35                  40                  45

Arg Met Arg Trp Leu Asn Tyr Leu Lys Pro Asn Val Lys Arg Gly Gln
50                  55                  60

Phe Ser Val Asp Glu Val Asp Leu Ile Ile Arg Leu His Lys Leu Leu
65                  70                  75                  80

Gly Asn Arg Trp Ser Leu Ile Ala Gly Arg Leu Ser Gly Arg Thr Ala
                85                  90                  95

Asn Asp Val Lys Asn Tyr Trp Asn Ser Asn Gln Arg Lys Lys Val Ile
            100                 105                 110

Ser Ser Thr Asp Glu Val Arg Ser Lys Pro Glu Ala Lys Ser Ile Thr
        115                 120                 125

Arg Asp Asn Ile Ile Lys Pro Gln Pro Trp Lys Phe Arg Ser Leu Phe
    130                 135                 140

Trp Leu Arg Gly Lys Ser Thr Pro Leu Ile Asn Val Gly Asn Ser Gln
145                 150                 155                 160

Tyr Gly Asn Asp Leu Cys Lys Ser Cys Tyr Ser Thr Val Ser Pro Pro
                165                 170                 175

Ser Asp Ile Asn Glu Val Glu Ser Leu Trp Trp Glu Ser Ser Leu Asp
            180                 185                 190

Asp Lys Glu Ile Asn Gln Thr Ile Asn Ser Ser Cys Leu Gly Ser Val
        195                 200                 205

Ser Ala Ala Ala Ala Ala Ala Tyr Pro Glu Ser Ser Glu Ser His Phe
```

```
                      210                 215                 220
Val Lys Asn Asn Ala Pro Gly Gly Ile Lys Thr Gly Asp Val Phe Tyr
225                 230                 235                 240

Glu Gln Gly Gln Asn Cys Trp Ser Asp Ile Ser Leu Asp Ala Asp Leu
                    245                 250                 255

Trp Asn Leu Ile Asn Thr Glu Leu Asp Gln Gln Gln Pro Glu Gly Leu
                260                 265                 270

Gln Ser Ile Met Leu
            275

<210> SEQ ID NO 7
<211> LENGTH: 249
<212> TYPE: PRT
<213> ORGANISM: Ipomoea batatas
<220> FEATURE:
<221> NAME/KEY: MISC_FEATURE
<223> OTHER INFORMATION: IbMYB1

<400> SEQUENCE: 7

Met Val Ile Ser Ser Val Trp Ser Gly Ser Ser Arg Val Arg Lys
1               5                   10                  15

Gly Ser Trp Ser Glu Glu Glu Asp Gln Leu Leu Arg Glu Cys Ile Gln
                20                  25                  30

Lys Tyr Gly Glu Gly Lys Trp His Leu Ile Pro Leu Arg Ala Gly Leu
            35                  40                  45

Asn Arg Cys Arg Lys Ser Cys Arg Leu Arg Trp Leu Asn Tyr Leu Arg
        50                  55                  60

Pro Asp Ile Lys Arg Gly Glu Phe Ser Pro Asp Glu Ile Asp Leu Ile
65                  70                  75                  80

Leu Arg Leu His Arg Leu Leu Gly Asn Arg Trp Ser Leu Ile Ala Gly
                85                  90                  95

Arg Ile Pro Gly Arg Thr Ala Asn Asp Val Lys Asn Leu Trp Asn Thr
            100                 105                 110

His Leu Gln Lys Lys Val Ser Ala Met Ala Ser Ser Arg Gln Asp Asn
        115                 120                 125

Tyr Trp Lys Gly Lys Ala Pro Glu Ile Thr Glu Asn Thr Val Val Arg
130                 135                 140

Pro Arg Pro Arg Arg Phe Leu Lys Ala Ser Ser Ser Pro Thr Thr Leu
145                 150                 155                 160

Leu Thr Gly Asn Ala Thr Met Val Ala Tyr Asp Gly Gln Leu Gln Glu
                165                 170                 175

His Met Thr Thr Gln Pro Glu Thr Thr Ser Asp Leu Leu Met Glu Asn
            180                 185                 190

Val Gln Gln Lys Asn Leu Thr Thr Leu Pro Ser Ala Leu Glu Thr
        195                 200                 205

Thr Pro His Asp Asn Val Lys Trp Trp Glu Asp Val Leu Ser Asp Lys
210                 215                 220

Glu Leu Asn Glu Glu Gly Gln Ile Cys Trp Ser Glu Phe Pro Thr Asp
225                 230                 235                 240

Ile Asp Leu Leu Ser Glu Leu Leu Ser
                245

<210> SEQ ID NO 8
<211> LENGTH: 250
<212> TYPE: PRT
<213> ORGANISM: Vitis vinifera
<220> FEATURE:
```

<221> NAME/KEY: MISC_FEATURE
<223> OTHER INFORMATION: VvMYBA1

<400> SEQUENCE: 8

Met Glu Ser Leu Gly Val Arg Lys Gly Ala Trp Ile Gln Glu Glu Asp
1               5                   10                  15

Val Leu Leu Arg Lys Cys Ile Glu Lys Tyr Gly Glu Gly Lys Trp His
            20                  25                  30

Leu Val Pro Leu Arg Ala Gly Leu Asn Arg Cys Arg Lys Ser Cys Arg
        35                  40                  45

Leu Arg Trp Leu Asn Tyr Leu Lys Pro Asp Ile Lys Arg Gly Glu Phe
    50                  55                  60

Ala Leu Asp Glu Val Asp Leu Met Ile Arg Leu His Asn Leu Leu Gly
65                  70                  75                  80

Asn Arg Trp Ser Leu Ile Ala Gly Arg Leu Pro Gly Arg Thr Ala Asn
                85                  90                  95

Asp Val Lys Asn Tyr Trp His Ser His His Phe Lys Lys Glu Val Gln
            100                 105                 110

Phe Gln Glu Glu Gly Arg Asp Lys Pro Gln Thr His Ser Lys Thr Lys
        115                 120                 125

Ala Ile Lys Pro His Pro His Lys Phe Ser Lys Ala Leu Pro Arg Phe
    130                 135                 140

Glu Leu Lys Thr Thr Ala Val Asp Thr Phe Asp Thr Gln Val Ser Thr
145                 150                 155                 160

Ser Arg Lys Pro Ser Ser Thr Ser Pro Gln Pro Asn Asp Asp Ile Ile
                165                 170                 175

Trp Trp Glu Ser Leu Leu Ala Glu His Ala Gln Met Asp Gln Glu Thr
            180                 185                 190

Asp Phe Ser Ala Ser Gly Glu Met Leu Ile Ala Ser Leu Arg Thr Glu
        195                 200                 205

Glu Thr Ala Thr Gln Lys Lys Gly Pro Met Asp Gly Met Ile Glu Gln
    210                 215                 220

Ile Gln Gly Gly Glu Gly Asp Phe Pro Phe Asp Val Gly Phe Trp Asp
225                 230                 235                 240

Thr Pro Asn Thr Gln Val Asn His Leu Ile
                245                 250

<210> SEQ ID NO 9
<211> LENGTH: 249
<212> TYPE: PRT
<213> ORGANISM: Arabidopsis thaliana
<220> FEATURE:
<221> NAME/KEY: MISC_FEATURE
<223> OTHER INFORMATION: AtPAP2

<400> SEQUENCE: 9

Met Glu Gly Ser Ser Lys Gly Leu Arg Lys Gly Ala Trp Thr Ala Glu
1               5                   10                  15

Glu Asp Ser Leu Leu Arg Leu Cys Ile Asp Lys Tyr Gly Glu Gly Lys
            20                  25                  30

Trp His Gln Val Pro Leu Arg Ala Gly Leu Asn Arg Cys Arg Lys Ser
        35                  40                  45

Cys Arg Leu Arg Trp Leu Asn Tyr Leu Lys Pro Ser Ile Lys Arg Gly
    50                  55                  60

Arg Leu Ser Asn Asp Glu Val Asp Leu Leu Leu Arg Leu His Lys Leu
65                  70                  75                  80

```
Leu Gly Asn Arg Trp Ser Leu Ile Ala Gly Arg Leu Pro Gly Arg Thr
             85                  90                  95

Ala Asn Asp Val Lys Asn Tyr Trp Asn Thr His Leu Ser Lys Lys His
            100                 105                 110

Glu Ser Ser Cys Cys Lys Ser Lys Met Lys Lys Lys Asn Ile Ile Ser
            115                 120                 125

Pro Pro Thr Thr Pro Val Gln Lys Ile Gly Val Phe Lys Pro Arg Pro
            130                 135                 140

Arg Ser Phe Ser Val Asn Asn Gly Cys Ser His Leu Asn Gly Leu Pro
145                 150                 155                 160

Glu Val Asp Leu Ile Pro Ser Cys Leu Gly Leu Lys Lys Asn Asn Val
                165                 170                 175

Cys Glu Asn Ser Ile Thr Cys Asn Lys Asp Asp Glu Lys Asp Asp Phe
                180                 185                 190

Val Asn Asn Leu Met Asn Gly Asp Asn Met Trp Leu Glu Asn Leu Leu
                195                 200                 205

Gly Glu Asn Gln Glu Ala Asp Ala Ile Val Pro Glu Ala Thr Thr Ala
            210                 215                 220

Glu His Gly Ala Thr Leu Ala Phe Asp Val Glu Gln Leu Trp Ser Leu
225                 230                 235                 240

Phe Asp Gly Glu Thr Val Glu Leu Asp
                245

<210> SEQ ID NO 10
<211> LENGTH: 248
<212> TYPE: PRT
<213> ORGANISM: Arabidopsis thaliana
<220> FEATURE:
<221> NAME/KEY: MISC_FEATURE
<223> OTHER INFORMATION: AtPAP1

<400> SEQUENCE: 10

Met Glu Gly Ser Ser Lys Gly Leu Arg Lys Gly Ala Trp Thr Thr Glu
1               5                   10                  15

Glu Asp Ser Leu Leu Arg Gln Cys Ile Asn Lys Tyr Gly Glu Gly Lys
            20                  25                  30

Trp His Gln Val Pro Val Arg Ala Gly Leu Asn Arg Cys Arg Lys Ser
            35                  40                  45

Cys Arg Leu Arg Trp Leu Asn Tyr Leu Lys Pro Ser Ile Lys Arg Gly
        50                  55                  60

Lys Leu Ser Ser Asp Glu Val Asp Leu Leu Arg Leu His Arg Leu Leu
65                  70                  75                  80

Leu Gly Asn Arg Trp Ser Leu Ile Ala Gly Arg Leu Pro Gly Arg Thr
                85                  90                  95

Ala Asn Asp Val Lys Asn Tyr Trp Asn Thr His Leu Ser Lys Lys His
            100                 105                 110

Glu Pro Cys Cys Lys Ile Lys Met Lys Lys Arg Asp Ile Thr Pro Ile
            115                 120                 125

Pro Thr Thr Pro Ala Leu Lys Asn Asn Val Tyr Lys Pro Arg Pro Arg
            130                 135                 140

Ser Phe Thr Val Asn Asn Asp Cys Asn His Leu Asn Ala Pro Pro Lys
145                 150                 155                 160

Val Asp Val Asn Pro Pro Cys Leu Gly Leu Asn Ile Asn Asn Val Cys
                165                 170                 175

Asp Asn Ser Ile Ile Tyr Asn Lys Asp Lys Lys Asp Gln Leu Val
                180                 185                 190
```

Asn Asn Leu Ile Asp Gly Asp Asn Met Trp Leu Glu Lys Phe Leu Glu
            195                 200                 205

Glu Ser Gln Glu Val Asp Ile Leu Val Pro Glu Ala Thr Thr Thr Glu
        210                 215                 220

Lys Gly Asp Thr Leu Ala Phe Asp Val Asp Gln Leu Trp Ser Leu Phe
225                 230                 235                 240

Asp Gly Glu Thr Val Lys Phe Asp
                245

<210> SEQ ID NO 11
<211> LENGTH: 246
<212> TYPE: PRT
<213> ORGANISM: Arabidopsis thaliana
<220> FEATURE:
<221> NAME/KEY: MISC_FEATURE
<223> OTHER INFORMATION: AtMYB113

<400> SEQUENCE: 11

Met Glu Gly Ser Pro Lys Gly Leu Arg Lys Gly Thr Trp Thr Thr Glu
1               5                   10                  15

Glu Asp Ile Leu Leu Arg Gln Cys Ile Asp Lys Tyr Gly Glu Gly Lys
            20                  25                  30

Trp His Arg Val Pro Leu Arg Thr Gly Leu Asn Arg Cys Arg Lys Ser
        35                  40                  45

Cys Arg Leu Arg Trp Leu Asn Tyr Leu Lys Pro Ser Ile Lys Arg Gly
    50                  55                  60

Lys Leu Cys Ser Asp Glu Val Asp Leu Val Leu Arg Leu His Lys Leu
65                  70                  75                  80

Leu Gly Asn Arg Trp Ser Leu Ile Ala Gly Arg Leu Pro Gly Arg Thr
                85                  90                  95

Ala Asn Asp Val Lys Asn Tyr Trp Asn Thr His Leu Ser Lys Lys His
            100                 105                 110

Asp Glu Arg Cys Cys Lys Thr Lys Met Ile Asn Lys Asn Ile Thr Ser
        115                 120                 125

His Pro Thr Ser Ser Ala Gln Lys Ile Asp Val Ile Lys Pro Arg Pro
    130                 135                 140

Arg Ser Phe Ser Asp Lys Asn Ser Cys Asn Asp Val Asn Ile Leu Pro
145                 150                 155                 160

Lys Val Asp Val Val Pro Leu His Leu Gly Leu Asn Asn Asn Tyr Val
                165                 170                 175

Cys Glu Ser Ser Ile Thr Cys Asn Lys Asp Glu Gln Lys Asp Lys Leu
            180                 185                 190

Ile Asn Ile Asn Leu Leu Asp Gly Asp Asn Met Trp Trp Glu Ser Leu
        195                 200                 205

Leu Glu Ala Asp Val Leu Gly Pro Glu Ala Thr Glu Thr Ala Lys Gly
    210                 215                 220

Val Thr Leu Pro Leu Asp Phe Val Gln Ile Trp Ala Arg Phe Asp Glu
225                 230                 235                 240

Glu Thr Leu Glu Leu Asn
                245

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 12
ttgacttgag gcatttggag                                                    20

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 13
caatggatag gtagcactgc                                                    20

<210> SEQ ID NO 14
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 14
gtacaagttt gtgagggaag aat                                                23

<210> SEQ ID NO 15
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 15
cacttgaact ggaactcgta ttac                                               24

<210> SEQ ID NO 16
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 16
actctgggac gtytggtaca                                                    20

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 17
gcttcataga tttacagtga                                                    20

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 18
tagtgaaatc agaaaagtct                                                    20

<210> SEQ ID NO 19

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 19
cgcaagtatt aaagaaataa                                                    20

<210> SEQ ID NO 20
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 20
tattcccaaa tcggcttctg g                                                  21

<210> SEQ ID NO 21
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 21
ggcaagcttg gctctcaggt c                                                  21

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 22
taaggacttg gctgagaaca                                                    20

<210> SEQ ID NO 23
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 23
atcagagtca ggaaggatgg                                                    20

<210> SEQ ID NO 24
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 24
aatacatggc accttcattg                                                    20

<210> SEQ ID NO 25
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 25
```
caaccttgct ggtacatcat                                        20

<210> SEQ ID NO 26
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 26
gtcacttkct gctaaatgga                                        20

<210> SEQ ID NO 27
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 27
gccaatcatt gactctagca                                        20

<210> SEQ ID NO 28
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 28
cgcaccagag actattcaag                                        20

<210> SEQ ID NO 29
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 29
tccaagtgta aggtctggtt                                        20

<210> SEQ ID NO 30
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 30
cctgacagca ctttcattga                                        20

<210> SEQ ID NO 31
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 31
acacgccaaa ttctcatcaa                                        20

<210> SEQ ID NO 32
<211> LENGTH: 20
<212> TYPE: DNA

```
<213> ORGANISM: Artificial Sequence
<220> FEATURE:
<223> OTHER INFORMATION: Synthetic oligonucleotide

<400> SEQUENCE: 32
ggtgacactr ttgagatctt                                                 20

<210> SEQ ID NO 33
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 33
ccatttcaac gacatasctt                                                 20

<210> SEQ ID NO 34
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 34
gcgacactgt tgagatcttg                                                 20

<210> SEQ ID NO 35
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 35
tcttgggtct tcctgaaaag                                                 20

<210> SEQ ID NO 36
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 36
caatcaatgg ccytgatgat                                                 20

<210> SEQ ID NO 37
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 37
tgtcgtccaa gaaaaagaga                                                 20

<210> SEQ ID NO 38
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 38
tttgcttctg aggatcctga                                                 20
```

<210> SEQ ID NO 39
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 39
tctcagctag tgtcttggag                                              20

<210> SEQ ID NO 40
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 40
caacaactcc atcttctcca                                              20

<210> SEQ ID NO 41
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 41
accaaacaac tcacctttct                                              20

<210> SEQ ID NO 42
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 42
ctaaggaagt gcgttgagaa                                              20

<210> SEQ ID NO 43
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 43
gccaagcaac ttgtgtagtc                                              20

<210> SEQ ID NO 44
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 44
aggtgcacta aggttttcct                                              20

<210> SEQ ID NO 45
<211> LENGTH: 20
<212> TYPE: DNA
<213> ORGANISM: Artificial Sequence
<220> FEATURE:

<223> OTHER INFORMATION: Synthetic oligonucleotide

<400> SEQUENCE: 45
tgaaactcat tccagtgtcc                                            20

<210> SEQ ID NO 46
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 46
gcaagaagat cagaagctca                                            20

<210> SEQ ID NO 47
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 47
agttcttcct ggcaatcttc                                            20

<210> SEQ ID NO 48
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 48
gccatctctc atcggaatgg aa                                         22

<210> SEQ ID NO 49
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 49
agggcagtga tttccttgct ca                                         22

<210> SEQ ID NO 50
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 50
tttgcatgct tcaatcgata accctctcta tcac                            34

<210> SEQ ID NO 51
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 51
tttggatcca tagcaacagt actcttgatg ttgt                            34

<210> SEQ ID NO 52
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 52
tttgcatgct tttcatagaa aatcatggag tcatg                              35

<210> SEQ ID NO 53
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 53
tttggatccg acaacaatag cactaatgat gtttt                              35

<210> SEQ ID NO 54
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 54
tttgcatgcg attaatgaaa agtc                                          24

<210> SEQ ID NO 55
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 55
tgtgtctttt tggatccgca gctagctctt tgaatgttc                          39

<210> SEQ ID NO 56
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 56
tttgcatgct taaatcttat ttactaacaa aacaat                             36

<210> SEQ ID NO 57
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 57
tttggatccg gcgaggtaca ctgagctctc                                    30

<210> SEQ ID NO 58
<211> LENGTH: 20
<212> TYPE: PRT
<213> ORGANISM: Artificial Sequence
<220> FEATURE:
<223> OTHER INFORMATION: Synthetic polypeptide
<220> FEATURE:

```
<221> NAME/KEY: MISC_FEATURE
<222> LOCATION: (1)..(1)
<223> OTHER INFORMATION: Xaa is D or E
<220> FEATURE:
<221> NAME/KEY: MISC_FEATURE
<222> LOCATION: (3)..(4)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa is R or K
<220> FEATURE:
<221> NAME/KEY: MISC_FEATURE
<222> LOCATION: (6)..(8)
<223> OTHER INFORMATION: Xaa is any amino acid
<220> FEATURE:
<221> NAME/KEY: MISC_FEATURE
<222> LOCATION: (10)..(15)
<223> OTHER INFORMATION: Xaa is any amino acid
<220> FEATURE:
<221> NAME/KEY: MISC_FEATURE
<222> LOCATION: (17)..(19)
<223> OTHER INFORMATION: Xaa is any amino acid

<400> SEQUENCE: 58

Xaa Leu Xaa Xaa Xaa Xaa Xaa Xaa Leu Xaa Xaa Xaa Xaa Xaa Xaa Leu
1               5                   10                  15

Xaa Xaa Xaa Arg
            20

<210> SEQ ID NO 59
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 59

Ala Asn Asp Val
1

<210> SEQ ID NO 60
<211> LENGTH: 7
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa is R or K
<220> FEATURE:
<221> NAME/KEY: MISC_FEATURE
<222> LOCATION: (3)..(3)
<223> OTHER INFORMATION: Xaa is any amino acid
<220> FEATURE:
<221> NAME/KEY: MISC_FEATURE
<222> LOCATION: (4)..(4)
<223> OTHER INFORMATION: Xaa is P, A, or R
<220> FEATURE:
<221> NAME/KEY: MISC_FEATURE
<222> LOCATION: (5)..(6)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa is F or Y

<400> SEQUENCE: 60

Xaa Pro Xaa Xaa Xaa Xaa Xaa
1               5
```

TRANSGENIC PLANTS FOR ENHANCING ANTHOCYANIN BIOSYNTHESIS

CROSS-REFERENCE TO RELATED APPLICATION

The present application claims the benefit of Korean Application No. 10-2015-0161304, filed Nov. 17, 2015, which is hereby incorporated by reference.

BACKGROUND

Technical Field

The present invention relates to a transgenic plant with enhanced anthocyanin biosynthesis. More specifically, the present invention relates to a transgenic plant with enhanced anthocyanin biosynthesis by the introduction of PtrMYB119 gene operably linked to a promoter, a method for preparing the transgenic plant, a method for producing anthocyanin from the transgenic plant, a composition for promoting anthocyanin biosynthesis including PtrMYB119 gene operably linked to a promoter, a kit for promoting anthocyanin biosynthesis including the composition, and a method for enhancing anthocyanin biosynthesis in a plant including introducing the composition into a plant for its expression.

Background Art

Plants are important sources from which nutrients required in daily life can be obtained. These nutrients and many other minerals are produced by various synthetic routes for secondary metabolites present in plants, and synthetic enzymes related thereto are also known to be closely associated with the synthesis of antibiotics and other materials for pharmaceutical drugs discovered in natural resource plants. Recently, studies were actively carried out toward the enhancement of secondary metabolites using useful plants by controlling their metabolic pathways or the synthesis of new materials.

There are about 400,000 plant species in existence on earth, but only about 10% of these are the subject of study. Nevertheless, most pharmacological components of importance have been extracted from plants for use, and some plants have been studied for more than two centuries. Currently, about 25% of the pharmaceutical drugs consumed by public consumers are known to be derived from plants and the values of plant-derived secondary metabolites based on drug prescriptions are estimated to reach about 30 billion US dollars. The secondary metabolites of plants utilize synthetic pathways which are derived from the synthetic pathways for the main metabolites, and they are called secondary metabolites because these pathways are not considered to be absolutely essential for the survival of plants, and in most cases, their contents in plants have been confirmed to be very low (less than 1% of dry weight of a plant). However, these secondary metabolites have important roles in increasing the opportunities for plants to survive without moving in continuously-changing, extremely harsh environments, and various kinds of materials belong to this category.

Anthocyanins, being water-soluble pigment glycoside compounds present in plants, are natural plant pigments that exhibit various colors of purple, red, blue, etc., based on the acid concentration of vacuoles, chemical structures of the pigment compounds, and the state in which they are bound to various kinds of metal ions. Anthocyanin biosynthesis in a plant is controlled by genetic factors possessed by the plant itself and the interaction of environmental factors that promote their expression (*The Plant Cell*, 7: 1071-1083). That is, the genes associated with anthocyanin biosynthesis are expressed by stimulation through light intensity, light quality, day length, temperature, moisture, chemical materials, and other factors (*Plant Physiol.* 92: 1191-1195; Planta, 194:541-549), and once the control genes are expressed, various kinds of enzymes associated with the biosynthesis process are produced and anthocyanins are prepared by the reactions thereof.

Recently, various physiological actions of anthocyanins were reported. For example, it was confirmed that anthocyanins have functions such as an anti-aging activity, an antibacterial activity, an antimutagenic activity, a cholesterol-lowering effect, a vision-improving effect, a blood vessel-protecting effect, an anti-ulcer effect, an anti-oxidative effect, etc. In particular, with respect to the anti-oxidative effect, anthocyanins were shown to have an anti-oxidative effect 5- to 7-fold higher than that of tocopherol, a natural antioxidant. Anthocyanins have low toxicities, and therefore, anthocyanins are used in the production of processed foods such as soft drinks, jams, vision-protecting beverages, candies, etc.; cosmetics; the dye industry; drug development; etc. Recently, anthocyanins were spotlighted as a safe natural coloring agent to replace synthetic coloring agents which are suspected of having carcinogenicity and hepatotoxicity, and are evaluated as a useful component which can provide visual freshness and pleasure, along with their importance in the aspect of food and nutrition.

Anthocyanins are widely present in various plants, and frequently contained in flowers, fruits, stems, leaves, roots, etc. of plants. Since anthocyanins can be extracted from plants such as grapes, strawberries, olives, red cabbages, eggplants, roses, etc. to be used as various raw materials, active studies are focused on improving the productivity of anthocyanins.

For example, Korean Patent Application Publication No. 2010-0022553 discloses a method for controlling anthocyanin biosynthesis, which includes culturing *Arabidopsis thaliana* having a mutation on the ethylene receptor gene or *Arabidopsis thaliana* having a mutation on the ethylene signaling-associated gene in sucrose-containing media under light irradiation; Korean Patent Application Publication No. 2010-0103189 discloses a medium composition for improving flavonoid synthesis in plants, which is characterized in that 200 mM to 300 mM sucrose is contained, and a method for producing flavonoid using the same; and Korean Patent Application Publication No. 2014-0126528 discloses a novel RsMYB1 isolated from crimson radish and the effect of improving the accumulated amount of anthocyanin pigment in a transgenic plant therefrom.

Under these circumstances, the present inventors have made efforts to develop a method for improving anthocyanin biosynthesis, and as a result, they have discovered that the level of anthocyanin biosynthesis was increased in a plant in which PtrMYB119 gene (a kind of R2R3 MYB gene) was overexpressed, thereby completing the present invention.

DISCLOSURE

Technical Problem

An object of the present invention is to provide a transgenic plant with enhanced anthocyanin biosynthesis, in which the plant is introduced with PtrMYB119 gene operably linked to a promoter.

Another object of the present invention is to provide a method for preparing the transgenic plant.

Still another object of the present invention is to provide a method for producing anthocyanin from the transgenic plant.

Still another object of the present invention is to provide a composition for promoting anthocyanin biosynthesis including PtrMYB119 gene operably linked to a promoter.

Still another object of the present invention is to provide a kit for promoting anthocyanin biosynthesis including the composition.

Still another object of the present invention is to provide a method for enhancing anthocyanin biosynthesis in a plant including introducing the composition to the plant.

Technical Solution

While conducting various studies to improve anthocyanin biosynthesis, the present inventors have focused their studies on the R2R3 MYB gene, which is known to regulate anthocyanin biosynthesis. In particular, among the R2R3 MYB genes derived from poplars, the PtrMYB119 gene is present on the $17^{th}$ chromosome, and as a result of sequence analysis, it was confirmed that the PtrMYB119 gene has a high homology with production of anthocyanin pigment 1 (PAP1) which is involved in anthocyanin biosynthesis in *Arabidopsis thaliana* and that it is phylogenetically located in a position similar to that of a gene which is known to be involved in anthocyanin biosynthesis in Petunia, tomatoes, sweet potatoes, grapes, etc.

In this regard, the effect of the overexpression of the PtrMYB119 gene was analyzed in a transgenic poplar where the PtrMYB119 gene was overexpressed. As a result, those cells in which anthocyanins were accumulated in a large amount were observed in the pith, cortex, phloem, ray cells, and cambium layer. In particular, it was confirmed that those cells, in which anthocyanins were accumulated in a large amount, were densely gathered in the outer layer of subcutaneous cells. However, it was confirmed that the level of flavonoid having a chemical structure similar to that of anthocyanin was not changed. Additionally, in the transgenic poplar where PtrMYB119 gene was overexpressed, it was confirmed that the expression levels of the genes involved in anthocyanin biosynthesis were increased. Furthermore, it was confirmed that even when anthocyanins were accumulated in a large amount, it did not have any effect on the growth of the transgenic plant.

As such, the technology which enables a high-yield production of anthocyanins in a plant by the overexpression of PtrMYB119 gene without affecting the growth of the plant has never been reported, and the present inventors are the first to develop the technology.

To achieve the above objects, in an aspect, the present invention provides a transgenic plant with enhanced anthocyanin biosynthesis, in which the plant is introduced with PtrMYB119 gene operably linked to a promoter to overexpress PtrMYB119 gene.

As used herein, the term "promoter" refers to a nucleotide sequence of DNA to which transcription factors can bind, and the promoter can bind to RNA polymerase mediated by a transcription factor and thereby induce transcription of open reading frame (ORF) located downstream thereof. In an exemplary embodiment of the present invention, 35S promoter was used.

As used herein, the term "operably linked" refers to a state in which a nucleic acid control sequence and a sequence encoding a target protein or RNA are functionally linked to each other to enable performing general functions. For example, a promoter and the nucleic acid sequence encoding a protein or RNA are operably linked to each other, and are thereby capable of affecting the expression of the coding sequence. The operable linkage with an expression vector can be prepared by a well-known gene recombination technology in the art, and site-specific DNA cleavage and linkage can be performed using the enzymes generally well-known in the art.

As used herein, the term "PtrMYB119 gene" refers to a gene for controlling anthocyanin biosynthesis, which is generally present on the $17^{th}$ chromosome of poplar plants, and the gene refers to a kind of the R2R3 MYB type gene. Information on the specific nucleotide sequence of the gene or the amino acid sequence of the protein is disclosed in NCBI (GenBank: NM_125275.1, NP_568891.1, etc.). In the present invention, a transgenic plant with enhanced anthocyanin biosynthesis was prepared using the PtrMYB119 gene having the nucleotide sequence of SEQ ID NO: 1.

As used herein, the term "anthocyanin" refers to a water-soluble pigment glucoside compound present in plants, which is a natural plant pigment that exhibits various colors of purple, red, blue, etc. based on the acid concentration of vacuoles, chemical structures of the pigment compounds, and the state in which it is bound to various kinds of metal ions. Known examples of the major anthocyanins detected from plants may include cyanidin, which is detected from apples, blackberries, peaches, etc.; pelargonidin, which is detected from strawberries, pomegranates, etc.; delphinidin, which is detected from eggplants, etc.; and peonidin, which is detected from mangos, etc. In the present invention, the levels of cyanidin and pelargonidin were measured for the confirmation of the anthocyanin level.

Meanwhile, anthocyanins are biosynthesized by a series of actions of various enzymes, which are expressed in plants, involved in the anthocyanin biosynthesis pathway. Known examples of the genes encoding each of the enzymes may include chalcone biosynthetic enzyme gene (PtrCHS1 and PtrCHS2), chalcone isomerase gene (PtrCHI1), flavonoid 3'-hydroxylase gene (PtrF3H1), dihydroflavonol reductase gene (PtrDFR1), anthocyanin biosynthetic enzyme gene (PtrANS1 and PtrANS2), etc. The transcription of each of the genes is known to be controlled by an R2R3 MYB type gene and a bHLH type gene.

When the PtrMYB119 gene is introduced into a target plant and overexpressed therein, it can promote the transcription of various anthocyanin biosynthesis genes, thereby promoting anthocyanin biosynthesis. Therefore, the composition including the PtrMYB119 gene, which is in a form to be operably linked to a promoter, can be used as a composition to promote anthocyanin biosynthesis in plants. In an exemplary embodiment, the composition may be an expression vector including the PtrMYB119 gene, which is operably linked to a promoter.

As used herein, the term "expression vector" refers to a recombinant vector which can express a target peptide in a target host cell, and it refers to a gene construct including essential control elements operably connected for the expression of the gene construct. The expression vector may include expression control elements such as an initiation codon, a termination codon, a promoter, an operator, etc. The start codon and the termination codon are generally considered as a part of the nucleotide sequence encoding a polypeptide, and they must essentially exert their actions in a subject when a gene construct is inserted thereinto and must be in frame with the coding sequence. The promoter of a vector may be constitutive or inducible. In the present invention, a transgenic plant with enhanced anthocyanin biosynthesis was prepared using an expression vector prepared by introducing the PtrMYB119 gene of SEQ ID NO: 1, which is operably linked to 35S promoter, into pK2GW7 vector.

Additionally, the expression vector may include a signal sequence for the release of a fusion polypeptide in order to promote the isolation of proteins from a cell culture. A specific initiation signal may also be necessary for efficient translation of the sequence of an inserted nucleic acid. These signals include the ATG initiation codon and neighboring sequences. In some cases, an exogenous translation control sequence that can include the ATG initiation codon may be provided. These exogenous translation control sequences and initiation codons may be various natural and synthetic supply sources. Expression efficiency may be increased by the introduction of an appropriate transcription- or translation-enhancing factor.

As used herein, the term "transformation" refers to a process of introducing DNA into a host cell and making the DNA to be replicable therein as a chromosomal factor or by completion of chromosomal integration. Specifically, in the present invention, transformation may refer to a process of introducing the PtrMYB119 gene to a host.

As used herein, the term "transgenic plant" refers to a plant which was produced by the transformation using a plant as the host.

In the present invention, the method of transformation may include any method to introduce a nucleic acid into an organism, a cell, a tissue, or an organ, and the transformation may be performed by selecting an appropriate standard technology according to plants as disclosed in the art. Examples of the method may include an electroporation, a protoplast fusion method, a CaPO$_4$ precipitation method, a CaCl$_2$ precipitation method, a stirring method using silicon carbide fiber, an agrobacteria-mediated transformation, PEG, dextran sulfate-, lipofectamine-, and dry/suppression-mediated transformations, etc., but are not limited thereto, and the method may preferably be an agrobacteria-mediated transformation.

For the purpose of the present invention, the transgenic plant can biosynthesize anthocyanins, and thus the transgenic plant may include both herbs and woody plants without limitation, as long as anthocyanin biosynthesis can be enhanced by the overexpression of the PtrMYB119 gene.

In an exemplary embodiment, examples of the herbs may include *Arabidopsis thaliana*, *Oryza sativa*; (rice), *Zea mays* (corns), *Miscanthus* sp. or *Pennisetum purpureum*, etc.; and examples of the woody plants may include *Eucalyptus* sp. (e.g., *E. alba*, *E. albens*, *E. amygdalina*, *E. aromaphloia*, *E. baileyana*, *E. balladoniensis*, *E. bicostata*, *E. botryoides*, *E. brachyandra*, *E. brassiana*, *E. brevistylis*, *E. brockwayi* *E. camaldulensis*, *E. ceracea*, *E. cloeziana*, *E. coccifera*, *E. cordata*, *E. cornuta*, *E. corticosa*, *E. crebra*, *E. croajingoleisis*, *E. curtisii*, *E. dalrympleana*, *E. deglupta*, *E. delegatensis*, *E. delicata*, *E. diversicolor*, *E. diversifolia*, *E. dives*, *E. dolichocarpa*, *E. dundasii*, *E. dunnii*, *E. elata*, *E. erythrocoiys*, *E. erythrophloia*, *E. eudesmoides*, *E. falcata*, *E. gamophylla*, *E. glaucina*, *E. globulus*, *E. globulus* subsp. *bicostata*, *E. globulus* subsp. *globulus*, *E. gongylocarpa*, *E. grandis*, *E. grandis×urophylla*, *E. guilfoylei*, *E. gunnii*, *E. hallii*, *E. houseana*, *E. jacksonii*, *E. lansdowneana*, *E. latisinensis*, *E. leucophloia*, *E. leucoxylon*, *E. lockyeri*, *E. lucasii*, *E. maidenii*, *E. marginata*, *E. megacarpa*, *E. melliodora*, *E. michaeliana*, *E. microcorys*, *E. microtheca*, *E. muelleriana*, *E. nitens*, *E. nitida*, *E. obliqua*, *E. obtusiflora*, *E. occidentalis*, *E. optima*, *E. ovata*, *E. pachyphylla*, *E. pauciflora*, *E. pellita*, *E. perriniana*, *E. petiolaris*, *E. pilularis*, *E. piperita*, *E. platyphylla*, *E. polyanthemos*, *E. populnea*, *E. preissiana*, *E. pseudoglobulus*, *E. pulchella*, *E. radiata*, *E. radiata* subsp. *radiata*, *E. regnans*, *E. risdoni*, *E. robertsonii* *E. rodwayi*, *E. rubida*, *E. rubiginosa*, *E. saligna*, *E. salmonophloia*, *E. scoparia*, *E. sieberi*, *E. spathulata*, *E. staeri* *E. stoatei*, *E. tenuipes*, *E. tenuiramis*, *E. tereticornis*, *E. tetragona*, *E. tetrodonta*, *E. tindaliae*, *E. torquata*, *E. umbra*, *E. urophylla*, *E. vernicosa*, *E. viminalis*, *E. wandoo*, *E. wetarensis*, *E. willisii*, *E. willisii* subsp. *falciformis*, *E. willisii* subsp. *willisii*, *E. woodwardii*), *Populus* sp. (e.g., *P. alba*, *P. alba×P. grandidentata*, *P. alba×P. tremula*, *P. alba× P. tremula* var. *glandulosa*, *P. alba×P. tremuloides*, *P. balsamifera*, *P. balsamifera* subsp. *trichocarpa*, *P. balsamifera* subsp. *trichocarpa×P. deltoides*, *P. ciliata*, *P. deltoides*, *P. euphratica*, *P. euramericana*, *P. kitakamiensis*, *P. lasiocarpa*, *P. laurifolia*, *P. maximowiczii*, *P. maximowiczii×P. balsamfera* subsp. *trichocarpa*, *P. nigra*, *P. sieboldii×P. grandideiztata*, *P. suaveolens*, *P. szechuanica*, *P. tomentosa*, *P. tremula*, *P. tremula×P. tremuloides*, *P. tremuloides*, *P. wilsonii*, *P. canadensis*, *P. yunnanensis*), conifers (e.g., loblolly pine (*Pinus taeda*), slash pine (*Pinus elliotii*), ponderosa pine (*Pinus ponderosa*), lodgepole pine (*Pinus contorta*), Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); silver fir (*Abies amabilis*); balsam fir (*Abies balsamea*)) and Japanese cedar (e.g., Western red cedar (*Thuja plicata*), Alaska yellow-cedar (*Chamecyparis nootkatensis*)), etc., but are not particularly limited thereto.

In another exemplary embodiment, the herb may be *Arabidopsis thaliana* and the woody plant may be poplar, but these are not particularly limited thereto.

As used herein, the term "*Arabidopsis thaliana*" is a flowering plant belonging to the genus *Brassicaceae*. Although the plant is not of agricultural significance, it is a very important plant widely used as a model plant in modern botany, and is very important for the studies of genetics and molecular biology. In the present invention, *Arabidopsis thaliana* may be used a representative herb plant, and specifically *Arabidopsis thaliana*, ecotype Columbia (Col-0), etc., may be used, but *Arabidopsis thaliana* is not particularly limited thereto.

As used herein, the term "poplar" is a collective term referring to plants belonging to the Family Salicaceae, Order Salicaceae of dicotyledon. In the present invention, the poplar may be used as the representative plant of woody plants, and it may be *Populus alba×P. tremula* var. *glandulosa*, etc., but is not particularly limited thereto.

According to an exemplary embodiment of the present invention, when the PtrMYB119 gene, among the R2R3 MYB genes derived from poplar, was introduced into *Arabidopsis thaliana*, there was an overall increase, instead of a particular region, in the level of red pigment in the plant, and this was assumed to have been caused by the increase in the anthocyanin production by the overexpression of the PtrMYB119 gene (FIG. 1A-B). As a result of the phylogenetic analysis using the sequence of the PtrMYB119 gene, it was confirmed that the gene belongs to the phylogeny of MYBs of dicotyledon, for the production of anthocyanin. As a result of the analysis of its conservative sequence, the PtrMYB119 gene was expected to be involved in anthocyanin biosynthesis (FIG. 2A-B).

In order to confirm the functions of the PtrMYB119 gene, a transgenic poplar introduced with the PtrMYB119 gene was prepared. As a result, it was confirmed that the transgenic poplar was red in its outer appearance (FIGS. 3A to 3C) and the expression level of the PtrMYB119 gene was increased 400-fold or higher (FIGS. 3D and 3E). Additionally, the contents of total flavonoid (FIG. 4A) and total phenol (FIG. 4B) increased, and accordingly, the antioxidative activity of the gene was also increased (FIG. 5). Furthermore, the expression levels of cyanidin and pelargonidin, which are kinds of anthocyanin, were increased in a range of 15- to 20-fold, respectively (FIG. 6A), but the level of flavonoid, which indicates UV absorptivity, was not increased (FIG. 6B), and thus it was analyzed that the PtrMYB119 gene has the effect of specifically promoting only the anthocyanin biosynthesis. HPLC analysis confirmed that cyanidin-3-O-glucoside is the major anthocyanin in the transgenic poplar (FIG. 7A-C).

As such, the expression levels of the genes involved in the anthocyanin biosynthesis pathway were compared. As a result, it was confirmed that the expression levels of the geneinvolved in the early stage of the flavonoid pathway, the gene involved in the anthocyanin biosynthesis, and the gene specifically involved in the proanthocyanin (PA) biosynthesis pathway were all increased (FIG. 8A-L). Additionally, it was confirmed that the amount of proanthocyanin production was increased in the transgenic poplar (FIG. 9A-B) and the expression level of the MYB134 gene, which is known as a positive control factor for the proanthocyanin biosynthesis, was shown to be similar to that of the control group; however, the expression level of the MYB182 gene, which is known as an inhibitor for the proanthocyanin/anthocyanin biosynthesis, was shown to be significantly reduced compared to that of the control group (FIG. 10A-B).

Lastly, as a result of the targets of the PtrMYB119 gene, it was confirmed that the direct downstream targets of the PtrMYB119 gene were shown to be PtrCHS1 gene and PtrANS2 gene (FIGS. 11A and 11B), and also it was confirmed that even when the level of anthocyanin synthesis increased, the levels of growth and photosynthesis of poplar did not change (FIG. 12A-F).

In still another aspect, the present invention provides a method for preparing a transgenic plant with enhanced anthocyanin biosynthesis, which includes introducing the PtrMYB119 gene, operably linked to a promoter, to a plant.

The promoter, PtrMYB119 gene, plant, anthocyanin, etc. are the same as described above, and the transgenic plant of the present invention can be prepared by the above method.

Additionally, the method may further include cultivating the transgenic plant, prepared by the above method, in soil or medium. In the present invention, the cultivation of the transgenic plant may be performed by a widely-known method and the cultivation conditions such as cultivation temperature, cultivation hours, and pH of medium, etc. may be appropriately adjusted.

The medium to be used must appropriately meet the required conditions for a particular transgenic plant. The types of the medium may include a solid medium, a liquid medium, and a double layer medium, and for components of the medium, water and a colloidal material (e.g., agar, agarose, gelite, etc.) may be used.

As inorganic nutrients, 15 elements, i.e., C, H, O, N, P, K, S, Ca, Mg, Fe, Mn, Cu, Zn, B, and Mo, may be added regardless of their form. As organic nutrients, carbohydrates, plant growth regulators, and vitamins may be added. As amino acids, myo-inositol, glycine, L-glutamine, etc., may be added.

As carbon sources, glucose, fructose, mannose, ribose, xylose, sucrose, melibiose, cellobiose, lactose, amylase, carbohydrates, raffinose, sorbitol, mannitol, glycerol, etc. may be added.

For example, in the present invention, *Arabidopsis thaliana* was cultivated in soil in a growth chamber at 25° C. (14 hours of light/10 hours of darkness) or in half-strength MS medium containing an appropriate antibiotic and 2% sucrose (Murashige and Skoog, Sigma) for screening. Additionally, the poplar used in the present invention (*Populus alba×P. tremula* var. *glandulosa*) was cultivated in the same conditions as for *Arabidopsis thaliana*.

In still another aspect, the present invention provides a method for producing anthocyanins including extracting anthocyanins from the transgenic plant in which the PtrMYB119 gene is introduced.

As described above, the transgenic plant provided in the present invention, in which the PtrMYB119 gene is introduced, showed a significantly increase level of anthocyanin biosynthesis, and thus the transgenic plant can be used as a raw material for the industrial production of anthocyanins. In particular, in the case of a transgenic poplar, the poplar not only has many leaves and a relatively large volume of leaves without any affect on the growth thereof, but also has rapid germination and growth rates. Therefore, the leaves of poplar can be used as a raw material for more economical production of anthocyanins.

The transgenic plant is the same as described above, and specifically, the leaves of the transgenic poplar can be used as a raw material for producing anthocyanins.

The process of extracting anthocyanins from the transgenic plant may be performed by a solvent extraction method, in which water and an alcohol having 1 to 4 carbon atoms may be used alone or in combination considering the characteristics of anthocyanins, which are hydrophilic glycosides, but is not particularly limited thereto, as long as anthocyanins can be extracted.

According to an exemplary embodiment of the present invention, it was confirmed that the poplar introduced with the PtrMYB119 gene produced a higher level of cyanidin and pelargonidin, which are the kinds of anthocyanins, compared to those of the tomatoes, red cabbages, blueberries, and cherries, which are the vegetables conventionally known to produce anthocyanins at high levels (FIG. 13), and thus the transgenic poplar, in which the PtrMYB119 gene was overexpressed, provided in the present invention can be used as a raw material for supplying anthocyanins.

In still another aspect, the present invention provides a composition for promoting anthocyanin biosynthesis including PtrMYB119 gene operably linked to a promoter.

The promoter, PtrMYB119 gene, anthocyanin, etc. are the same as described above and the anthocyanin biosynthesis can be promoted in any plant capable of biosynthesizing anthocyanins using the composition.

That is, the introduction of the PtrMYB119 gene included in the composition into a plant capable of biosynthesizing anthocyanins can increase the expression of various enzymes involved in the anthocyanin biosynthesis, and is thereby capable of promoting anthocyanin biosynthesis.

In still another aspect, the present invention provides a kit for promoting anthocyanin biosynthesis including the composition for promoting anthocyanin biosynthesis.

The kit of the present invention can promote anthocyanin biosynthesis in plants. The kit for promoting anthocyanin biosynthesis of the present invention may not only include the PtrMYB119 gene operably linked to a promoter, but also a composition suitable for the introduction or expression of the PtrMYB119 gene, containing one or more kinds of other components, a solution, or a device.

In an exemplary embodiment, the kit of the present invention may be a kit which includes essential elements necessary for performing the transformation of PtrMYB119 gene. For example, the kit may include a test tube or other appropriate container, a reaction buffer (pH and buffer concentration may vary), a container for cultivating plants, a medium for cultivating plants, sterile water, etc. Additionally, the kit may include a gene, which can be used as an internal control group, other than PtrMYB119 gene.

In still another aspect, the present invention provides a method for enhancing anthocyanin biosynthesis in a plant using the composition or kit.

Specifically, the method for enhancing anthocyanin biosynthesis of the present invention includes introducing the composition into a plant capable of biosynthesizing anthocyanin for expression. In particular, the promoter, PtrMYB119 gene, plant, anthocyanin, etc. are the same as described above, and the anthocyanin biosynthesis can be enhanced in any plant capable of biosynthesizing anthocyanins by the above method.

Advantageous Effects of the Invention

The use of the composition for enhancing anthocyanin biosynthesis provided in the present invention enables large-scale production of anthocyanins without any affect on the growth of the plant cell, which is a host, and thus the composition can be widely used for more effective production of anthocyanins.

DESCRIPTION OF DRAWINGS

FIG. 1A-B shows that transgenic plants exhibited high level accumulation of is red pigments. (1A) Transgenic *Arabidopsis* plants (10-day-old) overexpressing PtrMYB119 (35S::PtrMYB119) accumulates high level of red pigments compared to non-transformed control. Scale bars represent 1 mm. (1B) Magnified view of the red pigment accumulation in all parts of the 35S::PtrMYB119 *Arabidopsis* plant (1A). Scale bars represent 0.5 mm.

FIG. 2A-B shows that PtrMYB119 and PtrMYB120 belong to the R2R3-MYB family of TFs involved in anthocyanin biosynthesis. (2A) Phylogenetic analysis of the five poplar R2R3-MYB proteins identified in the present invention with selected R2R3-MYB proteins. Complete amino acid sequences were aligned using ClustalW and the rooted phylogenetic tree was constructed using MEGA 6.0 (Tamura et al. 2013) with the minimum evolution method (1000 bootstrap replicates) and p-distance model. Anthocyanin (AN) and proanthocyanidin (PA) biosynthetic subgroups are indicated. Human c-Myb and the root hair regulating subgroup (RH) were included as outgroups. (2B) Amino acid sequence alignment of the five poplar R2R3-MYB proteins with *Arabidopsis* (AtPAP1, AtPAP2 and AtMYB113), grape (VvMYBA1) and sweet potato (IbMYB1) R2R3-MYB proteins. The black bars indicate the R2 and R3 repeats of the MYB domain. The [D/E]Lx2[R/K]x3 Lx6Lx3R (SEQ ID NO: 58) motif necessary for interaction with bHLH TFs is indicated by the box in the R3 repeat. ANDV (SEQ ID NO: 59) and [R/K]Px[P/A/R]xx[F/Y] (SEQ ID NO: 60) motifs are indicated by the boxes.

FIG. 3A-E shows that overexpression of PtrMYB119 in a transgenic hybrid poplar resulted in high-level accumulation of red pigmentation. (3A) Transgenic poplars overexpressing PtrMYB119 (35S::PtrMYB119) had strong red-color pigmentation in whole plant relative to nontransformed control plants (control). Three independent transgenic poplar lines (e.g., #2, #3, and #4) and the control are shown. (3B) Red-colored pigmentation in the leaves of transgenic poplars. The 10th to 12th leaves from the top of transgenic poplars were arranged for comparison with control. (3C) Observation of red-colored pigmentation at the cellular level in stem cross sections of transgenic poplars and the control. Gray-colored arrows indicate red-colored cells. Ep, epidermis; Co, cortex; Ca, cambium; Pf, phloem fiber; Xy, xylem; Pi, pith. Scale bars represent 100 μm. (3D, 3E) Expression of the PtrMYB119 gene in the independent transgenic poplar lines compared with the control. First-strand cDNAs were synthesized from total RNA extracted from leaf tissues and used as template in semiquantitative RT-PCR (3D) or qRT-PCR (3E) experiments. Relative transcript levels were determined using the PtrACTIN2 gene as a quantitative control. Four-month-old poplars grown in a pot were used in these experiments. Error bars indicate standard deviations of three independent experiments. Note that red-colored pigmentations are shown in a darker tone in the black and white image.

FIG. 4A-B shows increased accumulation of total flavonoids and total phenolics in the 35S::PtrMYB119 transgenic poplars. (4A) Quantification of total flavonoid contents in the three independent 35S::PtrMYB119 poplar lines with control. Total flavonoids were determined using a calibration curve for quercetin as a standard and expressed as mg QE g-1 DW. (4B) Quantification of total phenolics in the three independent 35S::PtrMYB119 poplar lines with control. Total phenolics were determined using a calibration curve for gallic acid as a standard and expressed as mg GAE g-1 DW. Leaves of 2-month-old poplars grown in pots were used in these experiments. Error bars represent standard deviations of three independent experiments.

FIG. 5 shows that Antioxidant activities of 35S:: PtrMYB119 transgenic poplars were increased up to 103% (DPPH FRSA) and 55% (ABTS FRSA) compared to control poplars.

FIG. 6A-B shows massive accumulation of anthocyanins in 35S::PtrMYB119 transgenic poplars. (6A) Quantification of anthocyanin content in three independent 35S:: PtrMYB119 poplar lines and comparison with anthocyanin content in the control. Absorbance values of cyanidines (A530) and pelargonidines (A515) were plotted based on leaf fresh weight. (6B) Quantification of UV-absorptives in the three independent 35S::PtrMYB119 poplar lines and the control. Absorbance values of UV-absorptives (A330) were plotted based on leaf fresh weight. Two-month-old poplars grown in a pot were used in these experiments. Error bars indicate standard deviations of three independent experiments.

FIG. 7A-C shows that Accumulation of cyanidin-3-O-glucoside in 35S::PtrMYB119 transgenic poplars. Reverse-phase HPLC chromatogram monitored at 517 nm and UV-visible spectra of major anthocyanin peak (insets of (7A) and (7B)). (7A) Cyanidin-3-O-glucoside as a standard (10 μM). (7B) 35S::PtrMYB119 poplar line #2 (1 mg mL$^{-1}$). (7C) 35S::PtrMYB119 poplar line #2 (1 mg mL$^{-1}$) with cyanidin-3-O-glucoside standard (10 μM).

FIG. 8A-L shows expressional analysis of anthocyanin biosynthetic genes in 35S::PtrMYB119 transgenic poplars. (8A) PtrPAL1 (phenylalanine ammonialyase 1, Potri.006G126800.1), (8B) Ptr4CL2 (4-coumaroyl-CoA: ligase2, Potri.019G049500.2), (8C) PtrCHS1 (chalcone synthase1, Potri.014G145100.2), (8D) PtrCHS2 (chalcone synthase2, Potri.001G051500.1), (8E) PtrCHI1 (chalcone isomerase1, Potri.010G213000.1), (8F) PtrF3H1 (flavanone 3-hydroxylase1, Potri.005G113900.1), (8G) PtrDFR1 (dihydroflavonol reductase1, Potri.002G033600.1), (8H) PtrANS1 (anthocyanidin synthase1, Potri.003G119100.1), (8I) PtrANS2 (anthocyanidin synthase2, Potri.001G113100.1), (8J) PtrUFGT1 (UDP glucose: flavonoid-3-O-glucosyltransferase1, Potri.013G118700.1), (8K) PtrLAR1 (leucoanthocyanidin reductase1, Potri.008G116500.1), and (8L) PtrANR1 (anthocyanidin reductase1, Potri.004G030700.1). Quantitative real-time PCRs were performed using first-strand cDNA synthesized from total RNAs that were extracted from leaf tissues of 4-month-old poplars. Relative transcript levels were determined using the PtrACTIN2 gene as a quantitative control. Error bars indicate standard deviations of three independent experiments.

FIG. 9A-B shows that 35S::PtrMYB119 transgenic hybrid poplars accumulate more PAs than nontransformed control poplars. Proanthocyanidin accumulation in transgenic poplar expressing 35S::PtrMYB119. Dimethylaminocinnamaldehyde staining was used to investigate PA accumulation in the seventh internode of the stem (9A) and petioles (9B) of poplars, which were grown for 2 months at an LMO field after transplanting 4-month-old greenhouse grown poplars. Scale bars represent 100 µm.

FIG. 10A-B shows expression of MYB134 and MYB182 in 35S::PtrMYB119 transgenic poplars. (10A) MYB134 (Potri.006G221800.1) and (10B) MYB182 (Potri.004G088100.1). Quantitative real-time PCRs were performed using first-strand cDNA synthesized from total RNAs that were extracted from leaf tissues of 4-month-old poplars. Relative transcript levels were determined using the PtrACTIN2 gene as a quantitative control. Error bars indicate standard deviations of three independent experiments.

FIG. 11A-B shows that PtrMYB119 activates the expression of genes involved in anthocyanin biosynthesis in vivo. PtrMYB119 was coexpressed in *Arabidopsis* leaf protoplasts with the GUS reporter gene driven by the promoters of the PtrANS1, PtrANS2, and PtrCHS1 genes, together with PtrNAN for normalization. AtCesA4 promoter was used as a negative control. Activation of the promoter by PtrMYB119 was measured by assaying GUS activity after 16-h incubation. (11A) Diagram of the effector and reporter constructs used in this TAA. The effector construct contained the PtrMYB119 gene driven by the CaMV 35S promoter. The reporter constructs consisted of the GUS reporter gene driven by the promoters of the indicated genes. (11B) Transcriptional activation assay showing the effects of PtrMYB119 on induction of the promoters of PtrANS1, PtrANS2, and PtrCHS1. The expression level of the GUS reporter gene in the protoplast transfected with no effector was used as a control and was set to 1 after normalization. Error bars indicate standard errors of three biological replicates.

FIG. 12A-F shows that high-level accumulation of anthocyanin does not adversely affect the growth of 35S::PtrMYB119 transgenic hybrid poplars. Overall growth of three independent transgenic poplars grown for 2 months at an LMO field after transplanting 4-month-old greenhouse grown poplars was compared with nontransformed control. (12A) Height, (12B) diameter, (12C) number of internodes, (12D) leaf area, and (12E) shape and colors of leaves. Fifth to seventh leaves from the top are shown. (12F) Measurement of fluorescence (Fv/Fm) from poplar leaves grown for 4 months in a greenhouse. Error bars indicate standard deviations of three independent experiments.

FIG. 13 shows comparative analysis of anthocyanin quantity in 35S::PtrMYB119 with that in various other plants. Anthocyanin and UV-absorptive contents were estimated by spectrophotometry according to Dong et al. (2001). Quantification and comparison of anthocyanin content in the 35S::PtrMYB119 poplar line (#4) with that in control poplar, tomato, red cabbage, blueberry, cherry, and purple sweet potato. Absorbance values of cyanidines (A530) and pelargonidines (A515) were plotted based on grams fresh weight.

FIG. 14 shows tissue-specific expression of the five poplar R2R3-MYB TFs. Tissue-specific expression of the five poplar R2R3-MYB TFs was plotted by using publicly available transcriptome data. SL, shoot apical meristem and leaf primordial; ML, mature leaf without major veins; BP, bark and mature phloem; DP, developing phloem; Ca, cambial zone; DX, developing xylem; MX, mature xylem (from Ko et al. (2012)); Mcat, male catkin; Fcat, female catkin (from Wilkins et al. 2009).

FIG. 15A-C shows expressional analysis of PtrPAL2, PtrC4H1 and Ptr4CL1 genes in 35S::PtrMYB119 transgenic poplar. (15A) PtrPAL2 (Potri.008G038200.1), (15B) PtrC4H1 (Potri.013G157900.1), (15C) Ptr4CL1 (Potri.001G036900.1). qRT-PCRs were performed using first-strand cDNA synthesized from total RNAs that were extracted from leaf tissues of four-month-old poplars. Relative transcript levels were determined using the PtrACTIN2 gene as a quantitative control. Error bars indicate standard deviations of three independent experiments.

DETAILED DESCRIPTION OF THE INVENTION

Hereinafter, the present invention will be described in more detail with reference to the following Examples. However, these Examples are for illustrative purposes only, and the invention is not intended to be limited by these Examples.

Materials and Methods

1: Plant Materials and Growth Conditions

*Arabidopsis thaliana*, ecotype Columbia (Col-0), was used in both wild-type and transgenic plant experiments. *Arabidopsis* were grown in soil in a growth room (14 h light; light intensity, 150 µmol m$^{-2}$ s$^{-1}$) at 23° C. or on half-strength Murashige and Skoog (MS) medium (Sigma-Aldrich Co., St Louis, Mo., USA) containing 2% sucrose with appropriate antibiotics for screening.

Hybrid poplars (*Populus alba×P. tremula* var. *glandulosa, clone* BH) were used as both the nontransformed control plants and transgenic plants in the present invention. Plants were acclimated in soil and grown in controlled conditions in a growth room (16 h light; light intensity, 150 µmol m$^{-2}$ s$^{-1}$; 24° C.).

2: Vector Construction and Production of Transgenic Poplars

Full-length cDNAs encoding PtrMYB119 was amplified by polymerase chain reaction (PCR) and inserted downstream of the 35S promoter in the pK2GW7 vector (Karimi et al. 2002) using the Gateway cloning system to produce 35S::PtrMYB119 constructs. The resulting constructs were verified by DNA sequencing, and the primers used in the present invention are listed in Table 1. Vector constructs were introduced into *Agrobacterium tumefaciens* strain C58, which was used to transform *Arabidopsis* and poplar by the floral-dip method (Clough and Bent 1998) and leaf disk transformation-regeneration method (Horsch et al. 1985, Choi et al. 2005), respectively. Transformed cells from poplar were selected on MS medium containing 1.0 mg l$^{-1}$ 2,4-dichlorophenoxyacetic acid, 0.01 mg l$^{-1}$ benzylaminopurine, 0.1 mg l$^{-1}$ 1-naphthylacetic acid (NAA), 500 mg l$^{-1}$ cefotaxime, and 50 mg l$^{-1}$ kanamycin. Shoots were regenerated from calli by transferring them to woody plant medium containing 1.0 mg l$^{-1}$ zeatin, 0.1 mg l$^{-1}$ benzyladenine and 0.01 mg l⁻¹ NAA. Throughout the experiments, cultures were maintained in a culture room at 25±2° C. and were provided with cool white fluorescent light (150 µmol m⁻²s⁻¹, 16 h photoperiod).

TABLE 1

Primers used in the present invention

| Gene Name | Gene I.D. | Primers | Sequence | Restriction site* |
|---|---|---|---|---|
| PtrPAL1 | Potri.006G126800.1 | FW | TTGACTTGAGGCATTTGGAG (SEQ ID NO: 12) | — |
|  |  | RV | CAATGGATAGGTAGCACTGC (SEQ ID NO: 13) |  |
| PtrPAL2 | Potri.008G038200.1 | FW | GTACAAGTTTGTGAGGGAAGAAT (SEQ ID NO: 14) |  |
|  |  | RV | CACTTGAACTGGAACTCGTATTAC (SEQ ID NO: 15) |  |
| PtrC4H1 | Potri.013G157900.1 | FW | ACTCTGGGACGTYTGGTACA (SEQ ID NO: 16) | — |
|  |  | RV | GCTTCATAGATTTACAGTGA (SEQ ID NO: 17) |  |
| Ptr4CL1 | Potri.001G036900.1 | FW | TAGTGAAATCAGAAAAGTCT (SEQ ID NO: 18) | — |
|  |  | RV | CGCAAGTATTAAAGAAATAA (SEQ ID NO: 19) |  |
| Ptr4CL2 | Potri.019G049500.2 | FW | TATTCCCAAATCGGCTTCTGG (SEQ ID NO: 20) |  |
|  |  | RV | GGCAAGCTTGGCTCTCAGGTC (SEQ ID NO: 21) |  |
| PtrCHS1 | Potri.014G145100.2 | FW | TAAGGACTTGGCTGAGAACA (SEQ ID NO: 22) | — |
|  |  | RV | ATCAGAGTCAGGAAGGATGG (SEQ ID NO: 23) |  |
| PtrCHS2 | Potri.001G051500.1 | FW | AATACATGGCACCTTCATTG (SEQ ID NO: 24) | — |
|  |  | RV | CAACCTTGCTGGTACATCAT (SEQ ID NO: 25) |  |
| PtrCHI1 | Potri.010G213000.1 | FW | GTCACTTKCTGCTAAATGGA (SEQ ID NO: 26) |  |
|  |  | RV | GCCAATCATTGACTCTAGCA (SEQ ID NO: 27) |  |
| PtrF3H1 | Potri.005G113900.1 | FW | CGCACCAGAGACTATTCAAG (SEQ ID NO: 28) | — |
|  |  | RV | TCCAAGTGTAAGGTCTGGTT (SEQ ID NO: 29) |  |
| PtrDFR1 | Potri.002G033600.1 | FW | CCTGACAGCACTTTCATTGA (SEQ ID NO: 30) | — |
|  |  | RV | ACACGCCAAATTCTCATCAA (SEQ ID NO: 31) |  |
| PtrANS1 | Potri.003G119100.1 | FW | GGTGACACTRTTGAGATCTT (SEQ ID NO: 32) |  |
|  |  | RV | CCATTTCAACGACATASCTT (SEQ ID NO: 33) |  |
| PtrANS2 | Potri.001G113100.1 | FW | GCGACACTGTTGAGATCTTG (SEQ ID NO: 34) |  |
|  |  | RV | TCTTGGGTCTTCCTGAAAAG (SEQ ID NO: 35) |  |
| PtrLAR1 | Potri.008G116500.1 | FW | CAATCAATGGCCYTGATGAT (SEQ ID NO: 36) |  |
|  |  | RV | TGTCGTCCAAGAAAAAGAGA (SEQ ID NO: 37) |  |
| PtrANR1 | Potri.004G030700.1 | FW | TTTGCTTCTGAGGATCCTGA (SEQ ID NO: 38) | — |
|  |  | RV | TCTCAGCTAGTGTCTTGGAG (SEQ ID NO: 39) |  |

TABLE 1-continued

Primers used in the present invention

| Gene Name | Gene I.D. | Primers | Sequence | Restriction site* |
|---|---|---|---|---|
| PtrUFGT1 | Potri.013G118700.1 | FW | CAACAACTCCATCTTCTCCA (SEQ ID NO: 40) | — |
|  |  | RV | ACCAAACAACTCACCTTTCT (SEQ ID NO: 41) |  |
| PtrMYB119 | Potri.017G125600.1 | FW | CTAAGGAAGTGCGTTGAGAA (SEQ ID NO: 42) | — |
|  |  | RV | GCCAAGCAACTTGTGTAGTC (SEQ ID NO: 43) |  |
| MYB134 | Potri.006G221800.1 | FW | AGGTGCACTAAGGTTTTCCT (SEQ ID NO: 44) |  |
|  |  | RV | TGAAACTCATTCCAGTGTCC (SEQ ID NO: 45) |  |
| MYB182 | Potri.004G088100.1 | FW | GCAAGAAGATCAGAAGCTCA (SEQ ID NO: 46) |  |
|  |  | RV | AGTTCTTCCTGGCAATCTTC (SEQ ID NO: 47) |  |
| PtrACTINT2 | Potri.019G010400.1 | FW | GCCATCTCTCATCGGAATGGAA (SEQ ID NO: 48) | — |
|  |  | RV | AGGGCAGTGATTTCCTTGCTCA (SEQ ID NO: 49) |  |
| Pro_PtrANS1 | Potri.003G119100.1 | FW | TTTgcatgcTTCAATCGATAACCC TCTCTATCAC (SEQ ID NO: 50) | SphI |
|  |  | RV | TTTggatccATAGCAACAGTACTC TTGATGTTGT (SEQ ID NO: 51) | BamHI |
| Pro_PtrANS2 | Potri.001G113100.1 | FW | TTTgcatgcTTTTCATAGAAAATC ATGGAGTCATG (SEQ ID NO: 52) | SphI |
|  |  | RV | TTTggatccGACAACAATAGCACT AATGATGTTTT (SEQ ID NO: 53) | BamHI |
| Pro_PtrCHS1 | Potri.014G145100.2 | FW | TTTgcatgcGATTAATGAAAAGTC TGTGTCTT (SEQ ID NO: 54) | SphI |
|  |  | RV | TTTggatccGCAGCTAGCTCTTTG AATGTTC (SEQ ID NO: 55) | BamHI |
| Pro_AtCesA4 | AT5G44030.1 | FW | TTTgcatgcTTAAATCTTATTTACT AACAAAACAAT (SEQ ID NO: 56) | SphI |
|  |  | RV | TTTggatccGGCGAGGTACACTGA GCTCTC (SEQ ID NO: 57) | BamHI |

3: Histological Analysis

Cross sections of poplar stem or petioles were prepared by hand-cutting and observed for anthocyanin pigment accumulation without staining. Proanthocyanidins were detected by staining sections for 10 min with dimethylaminocinnamaldehyde (DMACA) (1% [w/v] in ethanol: 6 N HCl, 1:1[v/v]). Images were captured using a microscope (CHB-213, Olympus, Tokyo, Japan) and camera (DCM900, Oplenic, Hangzhou, China).

4: RNA Extraction and qRT-PCR

Total RNAs were extracted using the cetyl trimethylammonium bromide (CTAB) method with slight modification (Logemann et al. 1987). In brief, plant tissues were ground into a fine powder using liquid nitrogen and mixed with CTAB buffer followed by phenol: chloroform: isoamyl alcohol (25:24:1) extraction. Isopropanol was added to the mixture to isolate RNA. One microgram of total RNA was reverse-transcribed to produce first-strand cDNA using the PrimeScript™ RT reagent kit (Takara, Otsu, Japan) following the manufacturer's instructions. A semiquantitative real-time PCR (RT-PCR) was performed as described (Lee et al. 2014). Quantitative real-time PCR (qRT-PCR) was performed using the CFX96™ Real-Time PCR Detection System (Bio-Rad, Hercules, Calif., USA) with iQ™ SYBR® Supermix (Bio-Rad). Poplar ACTIN2 gene was used as the internal quantitative control (Kim et al. 2011), and relative expression level was calculated by the $2^{-\Delta\Delta Ct}$ method (Pfaffl 2001). All primer sequences were designed using Primer3 software (http://fokker.wi.mit.edu). Sequences are provided in Table 1.

5: Transient TAA

Preparation of *Arabidopsis* leaf protoplasts and transient transfection of reporter and effector constructs were performed as described previously (Ko et al. 2009, 2012). For the effector constructs, full-length cDNA of PtrMYB119 was ligated between the CaMV 35S promoter and the nopaline synthase terminator after removing GUS from the pTrGUS vector. Reporter constructs were created by placing promoter fragments (Pro_PtrANS1, Pro_PtrANS2, Pro_PtrCHS1, and Pro_AtCesA4) in front of the GUS reporter gene after removing the 35S promoter from the pTrGUS vector. The primers used for PCR amplification of full-length genes and promoters are listed in Table 1. Plasmid DNA was prepared using a Plasmid Plus Maxi kit (QIAGEN, Valencia, Calif., USA), and 7 μg of reporter and 7 μg of effector plasmids were used for transfections. For internal control for GUS activity normalization, 1 µg of PtrNAN plasmid (Kirby and Kavanagh 2002) was added. Then, 15 µL of plasmid mixture (15 µg) and 200 µL of protoplasts were transferred to 2 mL microcentrifuge tubes following the procedure described by Yoo et al. (2007). β-Glucuronidase and NAN enzyme assays were performed according to Kirby and Kavanagh (2002). NAN and GUS activities were measured using MUN (Sigma-Aldrich Co.) and MUG (Sigma-Aldrich Co.) as substrates, respectively, against MU standards on a Hoefer TK 100 fluorometer (excitation: 355 nm, emission: 460). The ratio of GUS and NAN activities is represented as relative GUS/NAN units. Three biological replicates were used in the experiments.

6: Sample Preparation for Biochemical Analysis

Freeze-dried samples (leaf tissues of both transgenic and nontransgenic poplar plants) were ground with mortar and pestle. Ground samples (0.8 g) were extracted by 320 mL of methanol/water/acetic acid (79.6: 19.9: 0.5, v/v) for 3 h in a shaking incubator (25° C., 150 r.p.m.). The solvent was filtered through Whatman No. 1 filter paper (Whatman International Ltd, Maidstone, UK). Extraction procedures were repeated under the same conditions. The solvent was evaporated using a vacuum rotary evaporator (Eyela Co., Tokyo, Japan) at 40° C.

7: Quantification of Total Phenolics and Flavonoids

Contents of total phenolic compounds were determined by the method reported by Eom et al. (2009) with some modification. Extract and Folin-Ciocalteu's phenol reagent (20 µL) were added to 2.6 mL of distilled water. After 6 min, 2.0 mL of 7% $Na_2CO_3$ was added. After 90 min, the absorbance was measured at 750 nm using a spectrophotometer (S-4100; Scinco, Seoul, Korea). The content of total phenolics was determined using a calibration curve for gallic acid (Sigma-Aldrich Co.) as a standard and expressed as mg gallic acid equivalents (GAE) $g^{-1}$ DW. Contents of total flavonoids were determined by the method described by Zhishin et al. (1999) with some modification. Extract (0.5 mL) was mixed with 3.2 mL of distilled water. Then, 5% $NaNO_2$ (0.15 mL), 10% $AlCl_3$ (0.15 mL), and 1 M NaOH (1.0 mL) were added to the mixture. The absorbance of the mixture was measured at 510 nm using a spectrophotometer (S-4100; Scinco). The content of total flavonoids was determined using a calibration curve for quercetin (Sigma-Aldrich Co.) as the standard and expressed as mg quercetin equivalents (QE) $g^{-1}$ dry weight (DW).

8: Reverse-Phase HPLC Analysis for Anthocyanins

The extracts were analyzed by reverse-phase high-performance liquid chromatography (HPLC) (Waters 2695 Alliance HPLC, Waters Inc., Milford, Mass., USA) using an octadecylsilane column (Prontosil 120-5-C18-ace-EPS, Bischoff, Leonberg, Germany). The flow rate of mobile phase was 1.0 mL $min^{-1}$. The mobile phases were (i) 10% aqueous formic acid and (ii) 10% methanolic formic acid. Gradient elution was performed as follows: 12% to 25% of solvent B for 32 min and 25% to 60% of solvent B for 32 to 48 min. The injection volume of samples (3 mg $mL^{-1}$ of methanol) was 20 µL. Quantifications of cyanidin-3-O-glucoside in transgenic poplars were performed by using cyanidin-3-O-glucoside chloride (Chengdu SinoStandards Bio-Tech Co., Chengdu, China) as a standard. Peaks were monitored at 517 nm with a Waters 996 photodiode array detector (Waters Inc.). High-performance liquid chromatography grade solvents were used for mobile phases.

9: Measurement of Chlorophyll Fluorescence

To analyze the photosynthetic capacity of transgenic poplars, chlorophyll fluorescence ($F_v/F_m$) was measured using a Pocket PEA chlorophyll fluorometer (Hansatech, Reutlingen, Germany). The fifth to seventh leaves from poplars grown for 3 months in a greenhouse were placed in the dark for 15 min and then exposed to a strong flash beam. The ratio of variable to maximal fluorescence ($F_v/F_m$), which approximates the maximum efficiency of photosystem II, was then calculated from the measured normal yield of chlorophyll fluorescence (Bilger et al. 1995, Gao and Peng 2006).

10: Measurement of Growth Parameters of Poplar

Overall growth parameters of poplars grown for 2 months at living modified organism (LMO) sites (latitude 37.2N, longitude 126.9E) after transplanting 4-month-old greenhouse grown poplars were measured. Parameters assessed were stem height (measured height from top to bottom), diameter (measured stem thickness at 10 cm above the soil level using slide calipers), number of internodes (counted from top to bottom), and leaf area (measured on the 10 to to 12th leaves from the top using a LI-3100 area meter, LI-COR Biosciences, Lincoln, Nebr., USA).

11: Measurement of Antioxidant Activities of 35S::PtrMYB119

Quantification of antioxidant activities in the three independent 35S::PtrMYB119 poplar lines with control. Antioxidant activities were measured by using DPPH FRSA (free radical scavenging activity) and ABTS FRSA of leaf extracts. FRSA was determined as vitamin C equivalents (mg VCE/g DW of extract). Leaves of 2-month-old poplars grown in pots were used in these experiments. Error bars represent standard deviation of three independent experiments. DPPH, 1,1-diphenyl-2-picrylhydrazyl; ABTS, 2,2-azino-bis-3-ethylbenzothiazoline-6-sulfonic acid; DW, Dry Weight.

Results

1: Identification of Poplar MYB TFs that Positively Regulate Anthocyanin Biosynthesis A MYB TF (PtrMYB119) that positively regulates anthocyanin production was found when expressed under the control of the CaMV 35S promoter in transgenic *Arabidopsis* (FIGS. 1A and 1B). Nucleotide sequence analysis in the poplar genome database (Phytozome; http://phytozome.jgi.doe.gov/pz/portal.html) revealed that the PtrMYB119 gene is located in tandem on chromosome 17 with three more genes (PtrMYB116, PtrMYB117, and PtrMYB118), and all of these genes are homologous to each other. Further analysis revealed that PtrMYB119 is highly homologous to *Arabidopsis* PAP1, a well-known transcriptional activator of anthocyanin biosynthesis (FIG. 2A-B). Phylogenetic analysis showed that all four poplar MYB genes (PtrMYB116, PtrMYB117, PtrMYB118, and PtrMYB119) are in the same clade (denoted 'AN' in FIG. 2A) as dicot anthocyanin-producing MYBs, including Petunia hybrid Anthocyanin2 (PhAN2), tomato Anthocyanin1 (LeANT1), sweet potato MYB1 (IbMYB1), grape VvMYBA1, and *Arabidopsis* AtPAP1. The 'AN' clade is clearly separated from the 'PA' clade, which includes PA-producing MYBs such as AtTT2, VvMYBPA1, and PtrMYB134 (FIG. 2A). In a subsequent amino acid sequence alignment analysis, it was found that all five poplar MYBs have three conserved motifs identified in anthocyanin-producing R2R3-MYB TFs in plants (e.g., *Arabidopsis*, sweet potato, and grape), apart from the very well-conserved DNA-binding domain, referred to as the R2R3 domain (FIG. 2B). The first motif, [D/E]Lx2[R/K]× 3L×6L×3R (also known as the ID domain, Grotewold et al. 2000, Stracke et al. 2001, Zimmermann et al. 2004), is involved in the interaction with bHLH proteins, and it is present in the R3 domain of PtrMYBs. The second conserved motif, ANDV, is also found in the R3 domain of PtrMYBs. The ANDV motif was identified by Lin-Wang et al. (2010) in their comparative sequence analysis of anthocyanin-promoting MYBs of dicot plants. The [R/K]Px[P/A/R]xx[F/Y] motif, which has been found in the C-terminal region of anthocyanin-regulating MYBs (Lin-Wang et al. 2010), was conserved in all of the aligned sequences (FIG. 2B). Taken together, these sequence analyses suggested that PtrMYB119 belong to the R2R3-MYB family of TFs involved in anthocyanin biosynthesis, which is consistent with the result of Wilkins et al. (2009).

2: PtrMYB119 is Highly Expressed in Male Catkin Tissues

Tissue-specific expression of all five PtrMYBs was evaluated using previously generated poplar tissue-specific transcriptome data (Wilkins et al. 2009, Ko et al. 2012). There was no significant expression of any of the five PtrMYB genes in any of the tissues tested (e.g., shoot apical, leaf primordia, mature leaf and stem tissues) with the exception of male and female catkins (FIG. 14). All PtrMYBs were expressed at high levels in male catkins. Because male catkins have anthers with a strong red pigmentation (Wilkins et al. 2009), the expression data suggested that PtrMYB119 may have a functional role in anthocyanin accumulation.

3: 35S::PtrMYB119 Transgenic Hybrid Poplars Exhibit High-Level Accumulation of Anthocyanins To further characterize the molecular function of putative anthocyanin-producing MYB TFs of poplar, transgenic hybrid poplar lines overexpressing PtrMYB119 (i.e., 35S::PtrMYB119) were produced. As expected, significant changes in pigmentation were observed in all parts of 35S::PtrMYB119 transgenic hybrid poplars. Characterization of 35S::PtrMYB119 poplar lines was the focus of this report. For further comparative phenotypic analysis, two strong (i.e., #2 and #4) and one mild (i.e., #3) transgenic 35S::PtrMYB119 poplar lines were selected in terms of red-color pigmentation in stem and leaf tissues (FIGS. 3A and 3B). To visualize the accumulation of red pigments at the cellular level, stem cross sections were prepared and the tissue was observed without any staining. Compared with nontransformed control poplar cross sections, numerous red pigmented cells were found in the pith, cortex, phloem, ray cells, and even cambium layers of 35S::PtrMYB119 poplars (FIG. 3C). In particular, red pigments were concentrated in the outer layer of subepidermal cells, which explained the intense redness of the stem and leaves of 35S::PtrMYB119 poplar lines. Expression level of the PtrMYB119 gene in three selected lines (i.e., #2, #3, and #4) was analyzed by semiquantitative RT-PCR as well as qRT-PCR and compared with the nontransformed control poplar (FIGS. 3D and 3E). PtrMYB119 was upregulated by as much as 400-fold in the selected lines relative to nontransformed control poplar (FIG. 3E). However, the expression level of the PtrMYB119 gene in each line was not linearly correlated to the red phenotype. Total flavonoids and total phenolics were quantified using leaf tissues of 2-month-old poplars (FIG. 4A-B). The contents of total flavonoids were increased more than twofold in 35S::PtrMYB119 poplar line (#4) compared with nontransformed control poplars (FIG. 4A). Total phenolics were also increased significantly in transgenic lines compared with nontransformed control poplars (FIG. 4B). To characterize the chemical nature of the accumulated anthocyanin in transgenic lines, a reverse-phase HPLC was performed. Based on the UV-visible spectra, showing two peaks at 278.5 nm and 517 nm (FIG. 7A-C), the chemical identity of the accumulated anthocyanin was supposed to be a glucoside derivative of cyaniding as reported by Aguilar and Hernández-Brenes (2015) and Skaar et al. (2014). Using a cyanidin-3-O-glucoside as a standard, it was confirmed that a majority of the accumulated anthocyanin in the transgenic poplar is the cyanidin-3-O-glucoside (FIG. 4A-B). The reverse-phase HPLC chromatogram clearly showed a massive accumulation of cyanidin-3-O-glucoside in leaf tissues of 35S::PtrMYB119 poplar lines (e.g., 1.17 mg g$^{-1}$ dry weight (DW) of line #4), while no detectable cyanidin-3-O-glucoside was found in nontransformed control poplar (Table 2). These results demonstrated that PtrMYB119 is a positive regulator of anthocyanin biosynthesis in poplar trees and that the red pigmentation of 35S::PtrMYB119 transgenic poplars was caused by accumulation of cyanidin-3-O-glucoside.

TABLE 2

Quantification of cyanidine-3-O-glucoside from transgenic poplars. ND, not determined. Data are presented as mean ± standard deviation (n = 3).

| | | 35S::PtrMYB119 | | |
|---|---|---|---|---|
| | Control | 2 | 3 | 4 |
| Cyanidin-3-O-glucoside (mg g$^{-1}$ DW) | ND | 0.85 ± 0.01 | 0.32 ± 0.10 | 1.17 ± 0.19 |

4: Increased Antioxidant Activity in the 35S::PtrMYB119 Transgenic Poplars

The anti-oxidative activity of the 35S::PtrMYB119 transgenic poplar was shown to increase compared to that of the poplar in the control group by 103% (DPPH FRSA) and 55% (ABTS FRSA) (FIG. 5).

5: Expression of Genes in the Anthocyanin Biosynthesis Pathway is Upregulated in 35S::PtrMYB119 Transgenic Hybrid Poplars Anthocyanin accumulation has been shown to have a positive correlation with the expression of anthocyanin biosynthetic genes (Paz-Ares et al. 1987, Borevitz et al. 2000, Espley et al. 2007). Because the 35S::PtrMYB119 transgenic poplars exhibited highly enhanced anthocyanin accumulation (FIGS. 3A-E and 4A-B), the expression of genes involved in the anthocyanin biosynthesis pathway was quantified by qRT-PCR in three independent lines and compared with nontransformed control poplar (FIG. 8A-L). Expression of phenylalanine ammonialyase (PtrPAL1) and 4 coumarate CoA ligase (Ptr4CL2) genes, which are involved in the initial steps of the flavonoid pathway, was upregulated (FIGS. 8A and 8B), while no significant changes in PtrPAL2 and cinnamic acid 4-hydroxylase (PtrC4H1) expression were observed in 35S::PtrMYB119 transgenic poplars (FIG. 13). As expected, increased expression of anthocyanin biosynthetic genes such as chalcone synthase (PtrCHS1 and PtrCHS2), chalcone isomerase (PtrCHI1), flavonoid 3'-hydroxylase (PtrF3H1), dihydroflavonol reductase (PtrDFR1), anthocyanidin synthase (PtrANS1 and PtrANS2), and UDP glucose: flavonoid-3-O-glucosyltransferase (PtrUFGT1) was observed (FIGS. 8C to 8J). Among these genes, expression levels of PtrCHS1, which catalyzes the initial step of anthocyanin biosynthesis and PtrANS2, which catalyzes the last step of anthocyanin biosynthesis, were upregulated by greater than 300-fold. Taken together, these results suggested that overexpression of PtrMYB119 induced anthocyanin pigment production by elevating transcript levels of multiple anthocyanin biosynthetic genes.

6: 35S::PtrMYB119 Transgenic Hybrid Poplars Accumulate More PAs Than Nontransformed Control Poplars Interestingly, the leucoanthocyanidin reductase (PtrLAR1) and anthocyanidin reductase (PtrANR1) genes, which are specific to the PA branch of the pathway, were upregulated by up to 12-fold (i.e., PtrANR1) in the 35S::PtrMYB119 transgenic poplars. To examine whether the 35S::PtrMYB119 transgenic poplars accumulated more PAs, DMACA staining was performed, which is commonly used for PA detection (Xie et al. 2003). Proanthocyanidins are major flavonoids in poplars (Osier and Lindroth 2004, Miranda et al. 2007, Mellway et al. 2009), and blue coloration, linked to the presence of PA, was observed in the epidermal cell layers of stems and petioles of nontransformed control poplars (FIG. 9A-B). The 35S::PtrMYB119 transgenic poplars showed much stronger blue coloration than control poplars not only in epidermal cell layers, but also in cortex and pith cells (FIG. 9A-B). These results suggested that overexpression of PtrMYB119 affects PA biosynthesis positively in poplar. Since poplar MYB134 has been known as a specific and positive transcriptional regulator of PA biosynthesis (Mellway et al. 2009), expression of MYB134 in the 35S::PtrMYB119 transgenic poplars was quantified compared with a nontransformed control. The result showed no significant changes of MYB134 expression (FIG. 10A). Interestingly, expression of MYB182, a repressor of both anthocyanin and PA biosynthesis (Yoshida et al. 2015), was largely suppressed in all of the 35S::PtrMYB119 poplar lines (FIG. 10B).

7: PtrMYB119 Activates Reporter Gene Expression in Transfected Protoplasts

To further verify the strong upregulation of PtrCHS1 and PtrANS2 in 35S::PtrMYB119 transgenic poplars, the ability of PtrMYB119 to activate the promoters of these genes using transient transcriptional activation assays (TAAs), as described previously (Ko et al. 2009), was analyzed. To do this, the promoter regions (approx. 1 kb) of PtrCHS1 and PtrANS2 genes were used to drive β-glucuronidase (GUS) reporter gene expression using PtrMYB119 as an effector (FIG. 11A). It was found that PtrMYB119 strongly activated expression of all promoters tested, with the exception of the AtCesA4 promoter, which is involved in secondary wall-specific cellulose biosynthesis (Taylor et al. 2003, Ko et al. 2009). This was thus used as an internal negative control in the TAA experiments (FIG. 11A-B). Accordingly, when AtMYB46 was used as an effector, a master regulator of secondary wall biosynthesis (Ko et al. 2009), only AtCesA4 promoter was activated (data not shown). Consistent with the qRT-PCR results (FIG. 8A-L), PtrMYB119 activated both PtrCHS1 and PtrANS2 promoters by up to 30- and 20-fold more than control levels, respectively, but only upregulated the PtrANS1 promoter by fivefold (FIG. 11B). This result suggested that both PtrCHS1 and PtrANS2 may be direct downstream targets of PtrMYB119. To support this result, AtMYB46 was used as an effector, a master regulator of secondary wall biosynthesis, in this experiment and it was found that AtMYB46 activates only AtCesA4 promoter but not PtrCHS1, PtrANS1, and PtrANS2 promoters (data not shown).

8: High-Level Accumulation of Anthocyanin Does Not Have an Adverse Effect on the Growth of Hybrid Poplars The bright red colors of the entire plant body of the 35S::PtrMYB119 transgenic poplars were reminiscent of the autumnal tints that signal the end of the growing season. It was therefore hypothesized that transgenic poplars with high-level accumulation of anthocyanins would grow less than nontransformed controls. However, the overall growth of transgenic poplars that were grown for 2 months at an LMO field after transplantation of 4-month-old greenhouse grown poplars was comparable to that of nontransformed controls in terms of height, diameter, internode number, and leaf area (FIGS. 12A to 12D). In addition, chlorophyll fluorescence was measured from leaves to assess the efficiency of photosystem II photochemistry (Bilger et al. 1995, Willits and Peet 2001, Gao and Peng 2006, Kadir 2006). Resulting Fv/Fm ratios were not significantly different between transgenic poplars and nontransformed control poplars (FIG. 12F), although there were considerable changes of leaf colors (FIG. 12E). These results suggested that elevated accumulation of anthocyanins did not affect the growth of 35S::PtrMYB119 transgenic hybrid poplars adversely, at least within the observation period.

Those of ordinary skill in the art will recognize that the present invention may be embodied in other specific forms without departing from its spirit or essential characteristics. The described embodiments are to be considered in all respects only as illustrative and not restrictive. The scope of the present invention is, therefore, indicated by the appended claims rather than by the foregoing description. All changes which come within the meaning and range of equivalency of the claims are to be embraced within the scope of the present invention.

The invention claimed is:

1. A transgenic plant with enhanced anthocyanin biosynthesis, wherein the plant is introduced with a PtrMYB119 gene operably linked to a promoter to overexpress the PtrMYB119 gene, wherein the PtrMYB119 gene consists of the nucleotide sequence of SEQ ID NO: 1.

2. The transgenic plant of claim 1, wherein the promoter is a 35S promoter.

3. The transgenic plant of claim 1, wherein the anthocyanin is at least one compound selected from the group consisting of cyanidin, pelargonidin, delphinidin, and peonidin.

4. The transgenic plant of claim 1, wherein the transgenic plant is *Arabidopsis thaliana* or poplar.

5. A method for preparing a transgenic plant with enhanced anthocyanin biosynthesis comprising introducing a PtrMYB119 gene operably linked to a promoter to a plant, wherein the PtrMYB119 gene consists of the nucleotide sequence of SEQ ID NO: 1.

6. The method of claim 5, further comprising cultivating the transgenic plant in soil or medium.

7. A method for preparing anthocyanin comprising extracting anthocyanin from the transgenic plant of claim 1.

8. The method of claim 7, wherein the transgenic plant is poplar.

9. A composition for promoting anthocyanin biosynthesis comprising a PtrMYB119 gene operably linked to a promoter, wherein the PtrMYB119 gene consists of the nucleotide sequence of SEQ ID NO: 1.

10. The composition of claim 9, wherein the composition is an expression vector comprising the PtrMYB119 gene operably linked to a promoter.

11. A kit for promoting anthocyanin biosynthesis comprising the composition of claim 9.

12. A method for enhancing anthocyanin biosynthesis in a plant comprising introducing the composition of claim 9 into a plant to express a PtrMY119 gene, wherein the PtrMYB119 gene consists of the nucleotide sequence of SEQ ID NO: 1.

* * * * *